(12) United States Patent
Lipman et al.

(10) Patent No.: US 9,897,610 B2
(45) Date of Patent: Feb. 20, 2018

(54) CALIBRATION MATERIAL DELIVERY DEVICES AND METHODS

(71) Applicant: Intuity Medical, Inc., Sunnyvale, CA (US)

(72) Inventors: Kelley J. Lipman, Livermore, CA (US); Michael F. Tomasco, Morgan Hill, CA (US); Peter Uy-Vu Ly, San Jose, CA (US); Jennifer Y. Blomo, San Carlos, CA (US); Paul D. Reynolds, Palo Alto, CA (US); John F. Larkin, Monterey, CA (US); Robin S. Gaffney, Redwood City, CA (US); Kimberly J. Tansey, San Carlos, CA (US); Christopher L. Stewart, Santa Clara, CA (US); Raúl Escutia, Sunnyvale, CA (US); Robert W. Bowers, Cupertino, CA (US)

(73) Assignee: Intuity Medical, Inc., Fremont, CA (US)

( * ) Notice: Subject to any disclaimer, the term of this patent is extended or adjusted under 35 U.S.C. 154(b) by 465 days.

(21) Appl. No.: 14/557,327

(22) Filed: Dec. 1, 2014

(65) Prior Publication Data
US 2015/0153351 A1    Jun. 4, 2015

Related U.S. Application Data

(63) Continuation of application No. 12/957,215, filed on Nov. 30, 2010, now Pat. No. 8,919,605.
(Continued)

(51) Int. Cl.
*G01N 33/66* (2006.01)
*G01N 33/96* (2006.01)
(Continued)

(52) U.S. Cl.
CPC ........... *G01N 33/66* (2013.01); *A61B 5/1495* (2013.01); *B01L 3/523* (2013.01); *G01N 21/78* (2013.01);
(Continued)

(58) Field of Classification Search
CPC ......... G01N 33/66; G01N 33/96; G01N 21/78
See application file for complete search history.

(56) References Cited

U.S. PATENT DOCUMENTS

| 842,690 A | 1/1907 | Oswalt |
| D137,874 S | 5/1944 | Partridge |

(Continued)

FOREIGN PATENT DOCUMENTS

| CA | 2 201 530 A1 | 9/1997 |
| CA | 2402115 A1 | 9/2001 |

(Continued)

OTHER PUBLICATIONS

ADA Consensus Development Panel. (Jan.-Feb. 1987). "Consensus Statement on Self-Monitoring of Blood Glucose," *Diabetes Care* 10(1):95-99.
(Continued)

*Primary Examiner* — Toan Le
(74) *Attorney, Agent, or Firm* — Cooley LLP

(57) ABSTRACT

A device includes: a first portion configured to be grasped by the hand of the user, and a second portion defining a reservoir containing a control material, wherein the control material contains a target analyte in a known or predetermined concentration. Methods for verifying the accuracy of an analyte monitoring device include receiving control information from a test cartridge, transporting control material to an analysis site, determining the presence of the control material, analyzing the control material, and providing a pass or fail signal.

23 Claims, 23 Drawing Sheets

Related U.S. Application Data

(60) Provisional application No. 61/358,791, filed on Jun. 25, 2010, provisional application No. 61/265,247, filed on Nov. 30, 2009.

(51) Int. Cl.
| | |
|---|---|
| *A61B 5/1495* | (2006.01) |
| *B01L 3/00* | (2006.01) |
| *G01N 21/78* | (2006.01) |
| *G06F 19/00* | (2018.01) |
| *A61B 5/145* | (2006.01) |
| *G01N 27/327* | (2006.01) |
| *G01N 33/487* | (2006.01) |

(52) U.S. Cl.
CPC ......... *G01N 27/3274* (2013.01); *G01N 33/96* (2013.01); *G06F 19/3406* (2013.01); *G06F 19/366* (2013.01); *A61B 5/14532* (2013.01); *A61B 2560/0223* (2013.01); *A61B 2562/08* (2013.01); *B01L 2200/148* (2013.01); *B01L 2300/022* (2013.01); *B01L 2300/123* (2013.01); *B01L 2400/0481* (2013.01); *B01L 2400/0683* (2013.01); *G01N 27/3273* (2013.01); *G01N 33/48785* (2013.01); *G01N 2201/12707* (2013.01); *G01N 2496/80* (2013.01); *Y10T 436/10* (2015.01); *Y10T 436/107497* (2015.01)

(56) References Cited

U.S. PATENT DOCUMENTS

| | | | |
|---|---|---|---|
| 2,749,797 A | 3/1950 | Harks | |
| 3,092,465 A | 6/1963 | Adams, Jr. | |
| 3,310,002 A | 3/1967 | Wilburn | |
| 3,620,209 A | 11/1971 | Kravitz | |
| 3,623,475 A | 11/1971 | Sanz et al. | |
| 3,626,929 A | 12/1971 | Sanz et al. | |
| 3,630,957 A | 12/1971 | Rey | |
| D223,165 S | 3/1972 | Komendat | |
| 3,723,064 A | 3/1973 | Liotta | |
| 3,741,197 A | 6/1973 | Sanz et al. | |
| 3,961,898 A | 6/1976 | Neeley et al. | |
| 3,992,158 A | 11/1976 | Przybylowicz et al. | |
| 4,014,328 A | 3/1977 | Cluff et al. | |
| 4,042,335 A | 8/1977 | Clement | |
| 4,057,394 A | 11/1977 | Genshaw | |
| 4,109,655 A | 8/1978 | Chacornac | |
| 4,250,257 A | 2/1981 | Lee et al. | |
| 4,253,083 A | 2/1981 | Imamura | |
| 4,254,083 A | 3/1981 | Columbus | |
| 4,258,001 A | 3/1981 | Pierce et al. | |
| 4,260,257 A | 4/1981 | Neeley et al. | |
| 4,289,459 A | 9/1981 | Neeley et al. | |
| 4,311,792 A | 1/1982 | Avery | |
| 4,321,397 A | 3/1982 | Nix et al. | |
| 4,350,762 A | 9/1982 | DeLuca et al. | |
| 4,394,512 A | 7/1983 | Batz | |
| 4,414,975 A | 11/1983 | Ryder et al. | |
| 4,416,279 A | 11/1983 | Lindner et al. | |
| 4,418,037 A | 11/1983 | Katsuyama et al. | |
| 4,422,941 A | 12/1983 | Vaughan, Jr. et al. | |
| 4,429,700 A | 2/1984 | Thees et al. | |
| 4,627,445 A | 12/1986 | Garcia et al. | |
| 4,637,403 A | 1/1987 | Garcia et al. | |
| 4,637,406 A | 1/1987 | Guinn et al. | |
| 4,653,513 A | 3/1987 | Dombrowski | |
| 4,661,319 A | 4/1987 | Lape | |
| 4,702,261 A | 10/1987 | Cornell et al. | |
| 4,711,250 A | 12/1987 | Gilbaugh, Jr. et al. | |
| 4,737,458 A | 4/1988 | Batz et al. | |
| 4,749,655 A | 6/1988 | Monthony et al. | |
| 4,767,415 A | 8/1988 | Duffy | |
| 4,774,192 A | 9/1988 | Terminiello et al. | |
| 4,787,398 A | 11/1988 | Garcia et al. | |
| 4,790,979 A | 12/1988 | Terminiello et al. | |
| 4,794,926 A | 1/1989 | Munsch et al. | |
| 4,815,843 A | 3/1989 | Tiefenthaler et al. | |
| 4,829,470 A | 5/1989 | Wang | |
| 4,844,095 A | 7/1989 | Chiodo et al. | |
| 4,846,785 A | 7/1989 | Cassou et al. | |
| 4,887,306 A | 12/1989 | Hwang et al. | |
| 4,920,977 A | 5/1990 | Haynes | |
| 4,929,426 A | 5/1990 | Bodai et al. | |
| 4,930,525 A | 6/1990 | Palestrant | |
| 4,935,346 A | 6/1990 | Phillips | |
| 4,953,552 A | 9/1990 | De Marzo | |
| 4,966,646 A | 10/1990 | Zdeblick | |
| 4,983,178 A | 1/1991 | Schnell | |
| 4,995,402 A | 2/1991 | Smith | |
| 5,029,583 A | 7/1991 | Meserol | |
| 5,035,704 A | 7/1991 | Lambert et al. | |
| 5,049,487 A | 9/1991 | Phillips et al. | |
| 5,050,617 A | 9/1991 | Columbus et al. | |
| 5,059,394 A | 10/1991 | Phillips et al. | |
| 5,077,199 A | 12/1991 | Basagni et al. | |
| 5,094,943 A | 3/1992 | Siedel et al. | |
| 5,110,724 A | 5/1992 | Hewett | |
| 5,114,350 A | 5/1992 | Hewett | |
| 5,116,759 A | 5/1992 | Klainer et al. | |
| 5,131,404 A | 7/1992 | Neeley et al. | |
| 5,141,868 A | 8/1992 | Shanks et al. | |
| 5,145,565 A | 9/1992 | Kater et al. | |
| 5,146,437 A | 9/1992 | Boucheron | |
| 5,153,416 A | 10/1992 | Neeley | |
| 5,164,575 A | 11/1992 | Neeley et al. | |
| 5,166,498 A | 11/1992 | Neeley | |
| 5,174,291 A | 12/1992 | Schoonen et al. | |
| 5,176,632 A | 1/1993 | Bernardi | |
| 5,179,005 A | 1/1993 | Phillips et al. | |
| 5,183,741 A | 2/1993 | Arai et al. | |
| 5,196,302 A | 3/1993 | Kidwell | |
| 5,208,163 A | 5/1993 | Charlton et al. | |
| 5,213,966 A | 5/1993 | Vuorinen et al. | |
| 5,217,480 A | 6/1993 | Habar et al. | |
| 5,218,966 A | 6/1993 | Yamasawa | |
| 5,223,219 A * | 6/1993 | Subramanian | B01L 3/5027 210/451 |
| 5,228,972 A | 7/1993 | Osaka et al. | |
| 5,234,818 A | 8/1993 | Zimmermann et al. | |
| 5,241,969 A | 9/1993 | Carson et al. | |
| 5,251,126 A | 10/1993 | Kahn et al. | |
| D341,848 S | 11/1993 | Bigelow et al. | |
| 5,266,266 A | 11/1993 | Nason | |
| 5,269,800 A | 12/1993 | Davis, Jr. | |
| 5,275,159 A | 1/1994 | Griebel | |
| 5,278,079 A | 1/1994 | Gubinski et al. | |
| 5,279,294 A | 1/1994 | Anderson et al. | |
| 5,288,646 A | 2/1994 | Lundsgaard et al. | |
| 5,299,571 A | 4/1994 | Mastrototaro | |
| 5,301,686 A | 4/1994 | Newman | |
| 5,302,513 A | 4/1994 | Mike et al. | |
| 5,304,468 A | 4/1994 | Phillips et al. | |
| 5,306,623 A | 4/1994 | Kiser et al. | |
| 5,308,767 A | 5/1994 | Terashima | |
| 5,314,441 A | 5/1994 | Cusack et al. | |
| 5,320,607 A | 6/1994 | Ishibashi | |
| 5,354,537 A | 10/1994 | Moreno | |
| 5,360,595 A | 11/1994 | Bell et al. | |
| 5,368,047 A | 11/1994 | Suzuki et al. | |
| 5,383,512 A | 1/1995 | Jarvis | |
| 5,390,671 A | 2/1995 | Lord et al. | |
| 5,395,388 A | 3/1995 | Schraga | |
| 5,399,316 A | 3/1995 | Yamada | |
| 5,401,110 A | 3/1995 | Neeley | |
| 5,402,798 A | 4/1995 | Swierczek et al. | |
| 5,426,032 A | 6/1995 | Phillips et al. | |
| 5,441,513 A | 8/1995 | Roth | |
| 5,451,350 A | 9/1995 | Macho et al. | |
| 5,458,140 A | 10/1995 | Eppstein et al. | |
| 5,460,777 A | 10/1995 | Kitajima et al. | |
| 5,460,968 A | 10/1995 | Yoshida et al. | |
| 5,482,473 A | 1/1996 | Lord et al. | |

(56) References Cited

U.S. PATENT DOCUMENTS

| | | |
|---|---|---|
| 5,506,200 A | 4/1996 | Hirschkoff et al. |
| 5,507,288 A | 4/1996 | Böcker et al. |
| 5,508,200 A | 4/1996 | Tiffany et al. |
| 5,510,266 A | 4/1996 | Bonner et al. |
| 5,514,152 A | 5/1996 | Smith |
| 5,525,518 A | 6/1996 | Lundsgaard et al. |
| 5,527,892 A | 6/1996 | Borsotti et al. |
| 5,563,042 A | 10/1996 | Phillips et al. |
| 5,568,806 A | 10/1996 | Cheney, II et al. |
| 5,569,287 A | 10/1996 | Tezuka et al. |
| 5,575,403 A | 11/1996 | Charlton et al. |
| 5,577,499 A | 11/1996 | Teves |
| 5,582,184 A | 12/1996 | Erickson et al. |
| 5,586,553 A | 12/1996 | Halili et al. |
| 5,591,139 A | 1/1997 | Lin et al. |
| 5,593,838 A | 1/1997 | Zanzucchi et al. |
| 5,611,809 A | 3/1997 | Marshall et al. |
| 5,624,458 A | 4/1997 | Lipscher |
| 5,630,986 A | 5/1997 | Charlton et al. |
| 5,632,410 A | 5/1997 | Moulton et al. |
| 5,636,632 A | 6/1997 | Bommannan et al. |
| 5,647,851 A | 7/1997 | Pokras |
| 5,658,515 A | 8/1997 | Lee et al. |
| 5,660,791 A | 8/1997 | Brenneman et al. |
| 5,670,031 A | 9/1997 | Hintsche et al. |
| 5,676,850 A | 10/1997 | Reed et al. |
| 5,680,858 A | 10/1997 | Hansen et al. |
| 5,681,484 A | 10/1997 | Zanzucchi et al. |
| 5,682,233 A | 10/1997 | Brinda |
| 5,697,901 A | 12/1997 | Eriksson |
| 5,700,695 A | 12/1997 | Yassinzadeh et al. |
| 5,701,181 A | 12/1997 | Boiarski et al. |
| 5,701,910 A | 12/1997 | Powles et al. |
| D389,761 S | 1/1998 | Thomas |
| 5,705,018 A | 1/1998 | Hartley |
| 5,708,247 A | 1/1998 | McAleer |
| 5,708,787 A | 1/1998 | Nakano et al. |
| 5,715,417 A | 2/1998 | Gardien et al. |
| 5,730,753 A | 3/1998 | Morita |
| 5,735,273 A | 4/1998 | Kurnik et al. |
| 5,736,103 A | 4/1998 | Pugh |
| 5,741,211 A | 4/1998 | Renirie et al. |
| 5,746,217 A | 5/1998 | Erickson et al. |
| 5,746,720 A | 5/1998 | Stouder, Jr. |
| 5,757,666 A | 5/1998 | Schreiber et al. |
| 5,759,364 A | 6/1998 | Charlton et al. |
| 5,766,066 A | 6/1998 | Ranniger |
| 5,771,890 A | 6/1998 | Tamada |
| 5,797,693 A | 8/1998 | Jaeger |
| 5,800,420 A | 9/1998 | Gross et al. |
| 5,801,057 A | 9/1998 | Smart et al. |
| 5,807,375 A | 9/1998 | Gross et al. |
| 5,820,570 A | 10/1998 | Erickson et al. |
| 5,827,183 A | 10/1998 | Kurnik et al. |
| 5,840,020 A | 11/1998 | Heinonen et al. |
| 5,841,126 A | 11/1998 | Fossum et al. |
| 5,843,692 A | 12/1998 | Phillips et al. |
| 5,846,837 A | 12/1998 | Thym et al. |
| 5,851,215 A | 12/1998 | Mawhirt et al. |
| 5,854,074 A | 12/1998 | Charlton et al. |
| D403,975 S | 1/1999 | Douglas et al. |
| 5,855,801 A | 1/1999 | Lin et al. |
| 5,856,195 A | 1/1999 | Charlton et al. |
| 5,858,194 A | 1/1999 | Bell |
| 5,866,281 A | 2/1999 | Guckel et al. |
| 5,871,494 A | 2/1999 | Simons et al. |
| 5,879,310 A | 3/1999 | Sopp et al. |
| 5,879,326 A | 3/1999 | Godshall et al. |
| 5,879,367 A | 3/1999 | Latterell et al. |
| 5,885,839 A | 3/1999 | Lingane et al. |
| 5,891,053 A | 4/1999 | Sesekura |
| 5,893,870 A | 4/1999 | Talen et al. |
| D411,621 S | 6/1999 | Eisenbarth et al. |
| 5,911,711 A | 6/1999 | Pelkey |
| 5,911,737 A | 6/1999 | Lee et al. |
| 5,912,139 A | 6/1999 | Iwata et al. |
| 5,925,021 A | 7/1999 | Castellano et al. |
| 5,928,207 A | 7/1999 | Pisano et al. |
| 5,930,873 A | 8/1999 | Wyser |
| 5,938,679 A | 8/1999 | Freeman et al. |
| 5,945,678 A | 8/1999 | Yanagisawa |
| 5,951,492 A | 9/1999 | Douglas et al. |
| 5,951,493 A | 9/1999 | Douglas et al. |
| 5,951,521 A | 9/1999 | Mastrototaro et al. |
| 5,954,685 A | 9/1999 | Tierney |
| 5,962,215 A | 10/1999 | Douglas et al. |
| 5,968,760 A | 10/1999 | Phillips et al. |
| 5,968,765 A | 10/1999 | Grage et al. |
| 5,968,836 A | 10/1999 | Matzinger et al. |
| 5,971,941 A | 10/1999 | Simons et al. |
| 5,972,294 A | 10/1999 | Smith et al. |
| 5,986,754 A | 11/1999 | Harding |
| 5,989,409 A | 11/1999 | Kurnik et al. |
| 5,993,189 A | 11/1999 | Mueller et al. |
| D417,504 S | 12/1999 | Love et al. |
| 6,001,067 A | 12/1999 | Shults et al. |
| 6,005,545 A | 12/1999 | Nishida et al. |
| 6,010,463 A | 1/2000 | Lauks et al. |
| 6,010,519 A | 1/2000 | Mawhirt et al. |
| 6,014,135 A | 1/2000 | Fernandes |
| 6,014,577 A | 1/2000 | Henning et al. |
| 6,023,629 A | 2/2000 | Tamada |
| 6,027,459 A | 2/2000 | Shain et al. |
| 6,030,827 A | 2/2000 | Davis et al. |
| 6,032,059 A | 2/2000 | Henning et al. |
| 6,036,924 A | 3/2000 | Simons et al. |
| 6,041,253 A | 3/2000 | Kost et al. |
| 6,045,753 A | 4/2000 | Loewy et al. |
| 6,048,352 A | 4/2000 | Douglas et al. |
| 6,050,988 A | 4/2000 | Zuck |
| 6,056,701 A | 5/2000 | Duchon et al. |
| 6,056,734 A | 5/2000 | Jacobsen et al. |
| 6,058,321 A | 5/2000 | Swayze et al. |
| 6,059,815 A | 5/2000 | Lee et al. |
| 6,061,128 A | 5/2000 | Zweig et al. |
| 6,063,039 A | 5/2000 | Cunningham et al. |
| 6,071,251 A | 6/2000 | Cunningham et al. |
| 6,071,294 A | 6/2000 | Simons et al. |
| 6,077,660 A | 6/2000 | Wong et al. |
| 6,080,116 A | 6/2000 | Erickson et al. |
| 6,083,196 A | 7/2000 | Trautman et al. |
| 6,086,544 A | 7/2000 | Hibner et al. |
| 6,090,790 A | 7/2000 | Eriksson |
| 6,091,975 A | 7/2000 | Daddona et al. |
| 6,093,156 A | 7/2000 | Cunningham et al. |
| 6,097,831 A | 8/2000 | Wieck et al. |
| 6,099,484 A | 8/2000 | Douglas et al. |
| 6,100,107 A | 8/2000 | Lei et al. |
| 6,102,933 A | 8/2000 | Lee et al. |
| 6,103,033 A | 8/2000 | Say et al. |
| 6,103,197 A | 8/2000 | Werner |
| 6,106,751 A | 8/2000 | Talbot et al. |
| 6,118,126 A | 9/2000 | Zanzucchi |
| 6,120,676 A | 9/2000 | Heller et al. |
| 6,123,861 A | 9/2000 | Santini, Jr. et al. |
| 6,126,899 A | 10/2000 | Woudenberg et al. |
| 6,132,449 A | 10/2000 | Lum et al. |
| 6,139,562 A | 10/2000 | Mauze et al. |
| 6,142,939 A | 11/2000 | Eppstein et al. |
| 6,152,942 A | 11/2000 | Brenneman et al. |
| 6,162,639 A | 12/2000 | Douglas |
| 6,172,743 B1 | 1/2001 | Kley et al. |
| 6,175,752 B1 | 1/2001 | Say et al. |
| 6,176,865 B1 | 1/2001 | Mauze et al. |
| 6,183,434 B1 | 2/2001 | Eppstein et al. |
| 6,183,489 B1 | 2/2001 | Douglas et al. |
| 6,187,210 B1 | 2/2001 | Lebouiz et al. |
| 6,192,891 B1 | 2/2001 | Gravel et al. |
| 6,193,873 B1 | 2/2001 | Ohara et al. |
| 6,200,296 B1 | 3/2001 | Dibiasi et al. |
| 6,206,841 B1 | 3/2001 | Cunningham et al. |
| 6,214,626 B1 | 4/2001 | Meller et al. |
| 6,219,574 B1 | 4/2001 | Cormier et al. |
| 6,228,100 B1 | 5/2001 | Schraga |

(56) References Cited

U.S. PATENT DOCUMENTS

| | | |
|---|---|---|
| 6,230,051 B1 | 5/2001 | Cormier et al. |
| 6,231,531 B1 | 5/2001 | Lum et al. |
| 6,241,862 B1 | 6/2001 | McAleer et al. |
| 6,242,207 B1 | 6/2001 | Douglas et al. |
| 6,245,215 B1 | 6/2001 | Douglas et al. |
| 6,251,083 B1 | 6/2001 | Yum et al. |
| 6,251,260 B1 | 6/2001 | Heller et al. |
| 6,254,586 B1 | 7/2001 | Mann et al. |
| 6,255,061 B1 | 7/2001 | Mori et al. |
| 6,256,533 B1 | 7/2001 | Yuzhakov et al. |
| 6,268,162 B1 | 7/2001 | Phillips et al. |
| 6,271,045 B1 | 8/2001 | Douglas et al. |
| 6,272,364 B1 | 8/2001 | Kurnik |
| 6,283,926 B1 | 9/2001 | Cunningham et al. |
| 6,289,230 B1 | 9/2001 | Chaiken et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,306,104 B1 | 10/2001 | Cunningham et al. |
| 6,309,351 B1 | 10/2001 | Kurnik et al. |
| D450,711 S | 11/2001 | Istvan et al. |
| 6,312,612 B1 | 11/2001 | Sherman et al. |
| 6,312,812 B1 | 11/2001 | Sherman et al. |
| 6,312,888 B1 | 11/2001 | Wong et al. |
| 6,315,738 B1 | 11/2001 | Nishikawa et al. |
| 6,322,808 B1 | 11/2001 | Trautman et al. |
| 6,329,161 B1 | 12/2001 | Heller et al. |
| 6,331,266 B1 | 12/2001 | Powell et al. |
| 6,332,871 B1 | 12/2001 | Douglas et al. |
| 6,334,856 B1 | 1/2002 | Allen et al. |
| 6,350,273 B1 | 2/2002 | Minagawa et al. |
| 6,352,514 B1 | 3/2002 | Douglas et al. |
| 6,356,776 B1 | 3/2002 | Berner et al. |
| 6,358,265 B1 | 3/2002 | Thorne, Jr. et al. |
| 6,364,890 B1 | 4/2002 | Lum et al. |
| 6,375,626 B1 | 4/2002 | Allen et al. |
| 6,375,627 B1 | 4/2002 | Mauze et al. |
| 6,379,969 B1 | 4/2002 | Mauze et al. |
| 6,391,005 B1 | 5/2002 | Lum et al. |
| 6,391,645 B1 | 5/2002 | Huang et al. |
| 6,402,704 B1 | 6/2002 | McMorrow |
| 6,409,679 B2 | 6/2002 | Pyo |
| 6,428,664 B1 | 8/2002 | BhulLar et al. |
| 6,449,608 B1 | 9/2002 | Morita et al. |
| 6,455,324 B1 | 9/2002 | Douglas |
| 6,493,069 B1 | 12/2002 | Nagashimada |
| 6,500,134 B1 | 12/2002 | Cassone |
| 6,520,973 B1 | 2/2003 | McGarry |
| 6,530,892 B1 | 3/2003 | Kelly |
| 6,537,243 B1 | 3/2003 | Henning et al. |
| 6,540,675 B2 | 4/2003 | Aceti et al. |
| 6,544,475 B1 | 4/2003 | Douglas et al. |
| 6,549,796 B2 | 4/2003 | Sohrab |
| 6,555,061 B1 | 4/2003 | Leong et al. |
| 6,558,624 B1 | 5/2003 | Lemmon et al. |
| 6,579,690 B1 | 6/2003 | Bonnecaze et al. |
| 6,589,260 B1 | 7/2003 | Schmelzeisen-Redeker et al. |
| 6,591,125 B1 | 7/2003 | Buse et al. |
| 6,602,205 B1 | 8/2003 | Erickson et al. |
| 6,612,111 B1 | 9/2003 | Hodges et al. |
| 6,616,616 B2 | 9/2003 | Fritz et al. |
| 6,626,874 B1 | 9/2003 | Duchamp |
| 6,656,167 B2 | 12/2003 | Numao et al. |
| 6,679,852 B1 | 1/2004 | Schmelzeisen-Redeker et al. |
| 6,706,000 B2 | 3/2004 | Perez et al. |
| 6,706,049 B2 | 3/2004 | Moerman |
| 6,706,159 B2 | 3/2004 | Moerman et al. |
| 6,707,554 B2 | 3/2004 | Miltner et al. |
| 6,740,800 B1 | 5/2004 | Cunningham |
| 6,743,635 B2 | 6/2004 | Neel et al. |
| 6,748,275 B2 | 6/2004 | Lattner et al. |
| 6,753,187 B2 | 6/2004 | Cizdziel et al. |
| 6,766,817 B2 | 7/2004 | da Silva |
| 6,793,633 B2 | 9/2004 | Douglas et al. |
| 6,830,669 B2 | 12/2004 | Miyazaki et al. |
| 6,836,678 B2 | 12/2004 | Tu |
| 6,837,858 B2 | 1/2005 | Cunningham et al. |
| 6,847,451 B2 | 1/2005 | Pugh |
| 6,849,052 B2 | 2/2005 | Uchigaki et al. |
| 6,896,850 B2 | 5/2005 | Subramanian et al. |
| 6,918,404 B2 | 7/2005 | Da Silva |
| 6,919,960 B2 | 7/2005 | Hansen et al. |
| 6,923,764 B2 | 8/2005 | Aceti et al. |
| 6,936,476 B1 | 8/2005 | Anderson et al. |
| D511,214 S | 11/2005 | Sasano et al. |
| 6,988,996 B2 | 1/2006 | Roe et al. |
| 7,004,928 B2 | 2/2006 | Aceti et al. |
| 7,011,630 B2 | 3/2006 | Desai et al. |
| 7,025,774 B2 | 4/2006 | Freeman et al. |
| D519,868 S | 5/2006 | Sasano et al. |
| 7,052,652 B2 | 5/2006 | Zanzucchi et al. |
| 7,066,586 B2 | 6/2006 | Da Silva |
| 7,066,890 B1 | 6/2006 | Lam et al. |
| 7,141,058 B2 | 11/2006 | Briggs et al. |
| 7,156,809 B2 | 1/2007 | Quy |
| 7,163,616 B2 | 1/2007 | Vreeke et al. |
| 7,192,061 B2 | 3/2007 | Martin |
| D540,343 S | 4/2007 | Cummins |
| 7,223,365 B2 | 5/2007 | Von Der Goltz |
| 7,225,008 B1 | 5/2007 | Ward et al. |
| 7,226,461 B2 | 6/2007 | Boecker et al. |
| 7,258,673 B2 | 8/2007 | Racchini et al. |
| D551,243 S | 9/2007 | Young |
| 7,270,970 B2 | 9/2007 | Anderson et al. |
| 7,297,151 B2 | 11/2007 | Boecker et al. |
| 7,299,081 B2 | 11/2007 | Mace et al. |
| 7,343,188 B2 | 3/2008 | Sohrab |
| 7,344,507 B2 | 3/2008 | Briggs et al. |
| 7,379,167 B2 | 5/2008 | Mawhirt et al. |
| 7,427,377 B2 | 9/2008 | Zanzucchi et al. |
| D580,068 S | 11/2008 | Shigesada et al. |
| D580,558 S | 11/2008 | Shigesada et al. |
| D599,373 S | 9/2009 | Kobayashi et al. |
| D601,257 S | 9/2009 | Berlinger |
| 7,585,278 B2 | 9/2009 | Aceti et al. |
| D601,444 S | 10/2009 | Jones et al. |
| D601,578 S | 10/2009 | Poulet et al. |
| 7,682,318 B2 | 3/2010 | Alden et al. |
| D622,393 S | 8/2010 | Gatrall et al. |
| 7,780,631 B2 | 8/2010 | Lum et al. |
| 7,803,123 B2 | 9/2010 | Perez et al. |
| 7,879,058 B2 | 2/2011 | Ikeda |
| 7,887,494 B2 | 2/2011 | Emery et al. |
| D642,191 S | 7/2011 | Barnett et al. |
| 7,988,644 B2 | 8/2011 | Freeman et al. |
| 8,012,103 B2 | 9/2011 | Escutia et al. |
| 8,012,104 B2 | 9/2011 | Escutia et al. |
| 8,105,849 B2 | 1/2012 | McDevitt et al. |
| D654,926 S | 2/2012 | Lipman et al. |
| 8,173,439 B2 | 5/2012 | Petrich et al. |
| 8,184,273 B2 | 5/2012 | Dosmann et al. |
| 8,231,832 B2 | 7/2012 | Zanzucchi et al. |
| 8,251,920 B2 | 8/2012 | Vreeke et al. |
| 8,298,255 B2 | 10/2012 | Conway et al. |
| 8,303,518 B2 | 11/2012 | Aceti et al. |
| 8,360,993 B2 | 1/2013 | Escutia et al. |
| 8,360,994 B2 | 1/2013 | Escutia et al. |
| 8,372,015 B2 | 2/2013 | Escutia et al. |
| 8,376,959 B2 | 2/2013 | Deck |
| 8,382,681 B2 | 2/2013 | Escutia et al. |
| 8,391,940 B2 | 3/2013 | Matzinger et al. |
| D691,174 S | 10/2013 | Lipman et al. |
| 8,574,168 B2 | 11/2013 | Freeman et al. |
| 8,628,721 B2 | 1/2014 | Eisenhardt et al. |
| 8,702,624 B2 | 4/2014 | Alden |
| 8,795,201 B2 | 8/2014 | Escutia et al. |
| 8,801,631 B2 | 8/2014 | Escutia et al. |
| 8,919,605 B2 | 12/2014 | Lipman et al. |
| 8,969,097 B2 | 3/2015 | Emery et al. |
| 9,060,723 B2 | 6/2015 | Escutia et al. |
| 9,060,727 B2 | 6/2015 | Saikley et al. |
| 9,095,292 B2 | 8/2015 | Zanzucchi et al. |
| 9,149,215 B2 | 10/2015 | Werner et al. |
| 9,366,636 B2 | 6/2016 | Emery et al. |

(56) References Cited

U.S. PATENT DOCUMENTS

| | | |
|---|---|---|
| 9,380,974 B2 | 7/2016 | Litherland et al. |
| 9,603,562 B2 | 3/2017 | Aceti et al. |
| 9,636,051 B2 | 5/2017 | Emery et al. |
| 2001/0001034 A1 | 5/2001 | Douglas |
| 2001/0027277 A1 | 10/2001 | Klitmose |
| 2001/0027328 A1 | 10/2001 | Lum et al. |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al. |
| 2002/0020688 A1 | 2/2002 | Sherman et al. |
| 2002/0022934 A1 | 2/2002 | Vogel et al. |
| 2002/0023852 A1 | 2/2002 | Mcivor et al. |
| 2002/0042594 A1 | 4/2002 | Lum et al. |
| 2002/0052618 A1 | 5/2002 | Haar et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0177764 A1 | 11/2002 | Sohrab |
| 2002/0183102 A1 | 12/2002 | Withers et al. |
| 2002/0188223 A1 | 12/2002 | Perez et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |
| 2003/0028125 A1 | 2/2003 | Yuzhakov et al. |
| 2003/0039587 A1 | 2/2003 | Niermann |
| 2003/0060730 A1 | 3/2003 | Perez |
| 2003/0083685 A1 | 5/2003 | Freeman et al. |
| 2003/0083686 A1 | 5/2003 | Freeman et al. |
| 2003/0105961 A1 | 6/2003 | Zatloukal et al. |
| 2003/0116596 A1 | 6/2003 | Terasawa |
| 2003/0135166 A1 | 7/2003 | Gonnelli |
| 2003/0135333 A1 | 7/2003 | Aceti |
| 2003/0143746 A1 | 7/2003 | Sage |
| 2003/0153844 A1 | 8/2003 | Smith et al. |
| 2003/0153900 A1 | 8/2003 | Aceti et al. |
| 2003/0175987 A1 | 9/2003 | Verdonk et al. |
| 2003/0206302 A1 | 11/2003 | Pugh |
| 2003/0207441 A1 | 11/2003 | Eyster et al. |
| 2003/0208113 A1 | 11/2003 | Mault et al. |
| 2003/0211619 A1 | 11/2003 | Olson et al. |
| 2003/0212344 A1 | 11/2003 | Yuzhakov et al. |
| 2003/0212345 A1 | 11/2003 | McAllister et al. |
| 2003/0212347 A1 | 11/2003 | Sohrab |
| 2003/0216628 A1 | 11/2003 | Bortz et al. |
| 2004/0010207 A1 | 1/2004 | Flaherty et al. |
| 2004/0030353 A1 | 2/2004 | Schmelzeisen-redeker et al. |
| 2004/0039303 A1 | 2/2004 | Wurster et al. |
| 2004/0049219 A1 | 3/2004 | Briggs et al. |
| 2004/0059256 A1 | 3/2004 | Perez |
| 2004/0072357 A1 | 4/2004 | Stiene et al. |
| 2004/0073140 A1 | 4/2004 | Douglas |
| 2004/0092842 A1 | 5/2004 | Boecker et al. |
| 2004/0092995 A1 | 5/2004 | Boecker et al. |
| 2004/0094432 A1 | 5/2004 | Neel et al. |
| 2004/0096959 A1 | 5/2004 | Stiene et al. |
| 2004/0097796 A1 | 5/2004 | Berman et al. |
| 2004/0098009 A1 | 5/2004 | Boecker et al. |
| 2004/0102803 A1 | 5/2004 | Boecker et al. |
| 2004/0122339 A1 | 6/2004 | Roe et al. |
| 2004/0132167 A1 | 7/2004 | Rule et al. |
| 2004/0138588 A1 | 7/2004 | Saikley et al. |
| 2004/0155084 A1 | 8/2004 | Brown |
| 2004/0157339 A1 | 8/2004 | Burke et al. |
| 2004/0178218 A1 | 9/2004 | Schomakers et al. |
| 2004/0186394 A1 | 9/2004 | Roe et al. |
| 2004/0191119 A1 | 9/2004 | Zanzucchi et al. |
| 2004/0199409 A1 | 10/2004 | Brown |
| 2004/0202576 A1 | 10/2004 | Aceti et al. |
| 2004/0209755 A1 | 10/2004 | Moore et al. |
| 2004/0230216 A1 | 11/2004 | LeVaughn et al. |
| 2004/0232180 A1 | 11/2004 | Badillo |
| 2004/0236251 A1 | 11/2004 | Roe et al. |
| 2004/0238675 A1 | 12/2004 | Banaszkiewicz et al. |
| 2004/0242982 A1 | 12/2004 | Sakata et al. |
| 2004/0249253 A1 | 12/2004 | Racchini et al. |
| 2004/0259180 A1 | 12/2004 | Burke et al. |
| 2005/0004494 A1 | 1/2005 | Perez et al. |
| 2005/0010134 A1 | 1/2005 | Douglas et al. |
| 2005/0015020 A1 | 1/2005 | LeVaughn et al. |
| 2005/0027182 A1 | 2/2005 | Siddiqui et al. |
| 2005/0038680 A1 | 2/2005 | McMahon |
| 2005/0070819 A1 | 3/2005 | Poux et al. |
| 2005/0096686 A1 | 5/2005 | Allen |
| 2005/0106713 A1 | 5/2005 | Phan et al. |
| 2005/0109386 A1 | 5/2005 | Marshall |
| 2005/0159678 A1 | 7/2005 | Taniike et al. |
| 2005/0187532 A1 | 8/2005 | Thurau et al. |
| 2005/0192492 A1 | 9/2005 | Cho et al. |
| 2005/0202567 A1 | 9/2005 | Zanzucchi et al. |
| 2005/0202733 A1 | 9/2005 | Yoshimura et al. |
| 2005/0209518 A1 | 9/2005 | Sage, Jr. et al. |
| 2005/0215872 A1 | 9/2005 | Berner et al. |
| 2005/0215923 A1 | 9/2005 | Wiegel |
| 2005/0234494 A1 | 10/2005 | Conway et al. |
| 2005/0244981 A1 | 11/2005 | Frey et al. |
| 2005/0245844 A1 | 11/2005 | Mace et al. |
| 2005/0255001 A1 | 11/2005 | Padmaabhan et al. |
| 2005/0277972 A1 | 12/2005 | Wong et al. |
| 2006/0008389 A1 | 1/2006 | Sacherer et al. |
| 2006/0036134 A1 | 2/2006 | Tarassenko et al. |
| 2006/0052724 A1 | 3/2006 | Roe |
| 2006/0064035 A1 | 3/2006 | Wang et al. |
| 2006/0094985 A1 | 5/2006 | Aceti et al. |
| 2006/0117616 A1 | 6/2006 | Jones et al. |
| 2006/0122536 A1 | 6/2006 | Haar et al. |
| 2006/0135873 A1 | 6/2006 | Karo et al. |
| 2006/0155317 A1 | 7/2006 | List |
| 2006/0161078 A1 | 7/2006 | Schraga |
| 2006/0178600 A1 | 8/2006 | Kennedy et al. |
| 2006/0189908 A1 | 8/2006 | Kennedy |
| 2006/0204399 A1 | 9/2006 | Freeman et al. |
| 2006/0229533 A1 | 10/2006 | Hoenes et al. |
| 2006/0241517 A1 | 10/2006 | Fowler et al. |
| 2006/0257993 A1 | 11/2006 | Mcdevitt et al. |
| 2006/0259102 A1 | 11/2006 | Slatkine |
| 2006/0281187 A1 | 12/2006 | Emery et al. |
| 2007/0016104 A1 | 1/2007 | Jansen et al. |
| 2007/0017824 A1 | 1/2007 | Rippeth et al. |
| 2007/0078313 A1 | 4/2007 | Emery et al. |
| 2007/0078358 A1 | 4/2007 | Escutia et al. |
| 2007/0083131 A1 | 4/2007 | Escutia et al. |
| 2007/0112281 A1 | 5/2007 | Olson |
| 2007/0149863 A1 | 6/2007 | Padmanabhan et al. |
| 2007/0179404 A1 | 8/2007 | Escutia et al. |
| 2007/0179405 A1 | 8/2007 | Emery et al. |
| 2007/0253531 A1 | 11/2007 | Okuzawa et al. |
| 2007/0255181 A1 | 11/2007 | Alvarez-icaza et al. |
| 2007/0255302 A1 | 11/2007 | Koeppel et al. |
| 2007/0274869 A1 | 11/2007 | Rannikko |
| 2008/0046831 A1 | 2/2008 | Imai et al. |
| 2008/0077048 A1 | 3/2008 | Escutia et al. |
| 2008/0135559 A1 | 6/2008 | Byrd |
| 2008/0139910 A1 | 6/2008 | Mastrototaro |
| 2008/0194934 A1 | 8/2008 | Ray et al. |
| 2008/0269625 A1 | 10/2008 | Halperin et al. |
| 2009/0018426 A1 | 1/2009 | Markle et al. |
| 2009/0054810 A1 | 2/2009 | Zanzucchi et al. |
| 2009/0156923 A1 | 6/2009 | Power et al. |
| 2009/0194432 A1 | 8/2009 | Deng |
| 2009/0292489 A1 | 11/2009 | Burke et al. |
| 2009/0301899 A1 | 12/2009 | Hodges et al. |
| 2010/0010374 A1 | 1/2010 | Escutia et al. |
| 2010/0021947 A1 | 1/2010 | Emery et al. |
| 2010/0021948 A1 | 1/2010 | Lipman et al. |
| 2010/0095229 A1 | 4/2010 | Dixon et al. |
| 2010/0174211 A1 | 7/2010 | Frey et al. |

(56) References Cited

U.S. PATENT DOCUMENTS

| | | |
|---|---|---|
| 2010/0185120 A1 | 7/2010 | Sacherer et al. |
| 2010/0217155 A1 | 8/2010 | Poux et al. |
| 2010/0331650 A1 | 12/2010 | Batman et al. |
| 2011/0098599 A1 | 4/2011 | Emery et al. |
| 2011/0105872 A1 | 5/2011 | Chickering et al. |
| 2011/0201909 A1 | 8/2011 | Emery et al. |
| 2012/0166090 A1 | 6/2012 | Lipman et al. |
| 2012/0296179 A1 | 11/2012 | Zanzucchi et al. |
| 2013/0110516 A1 | 5/2013 | Abulhaj et al. |
| 2013/0158430 A1 | 6/2013 | Aceti et al. |
| 2013/0158432 A1 | 6/2013 | Escutia et al. |
| 2013/0172698 A1 | 7/2013 | Reynolds et al. |
| 2013/0274568 A1 | 10/2013 | Escutia et al. |
| 2013/0274579 A1 | 10/2013 | Richter et al. |
| 2014/0316301 A1 | 10/2014 | Escutia et al. |
| 2014/0336480 A1 | 11/2014 | Escutia et al. |
| 2014/0376762 A1 | 12/2014 | Lipman et al. |
| 2015/0037898 A1 | 2/2015 | Baldus et al. |
| 2015/0212006 A1 | 7/2015 | Emery et al. |
| 2016/0038066 A1 | 2/2016 | Escutia et al. |
| 2016/0367178 A1 | 12/2016 | Emery et al. |
| 2017/0095188 A1 | 4/2017 | Emery et al. |

FOREIGN PATENT DOCUMENTS

| | | |
|---|---|---|
| CA | 2 513 465 A1 | 8/2004 |
| DE | 197 05 091 A1 | 2/1999 |
| DE | 199 22 413 A1 | 11/2000 |
| DE | 103 02 501 A1 | 8/2004 |
| EP | 0 103 426 A2 | 3/1984 |
| EP | 0 256 806 A2 | 2/1988 |
| EP | 0 396 016 A2 | 11/1990 |
| EP | 0 396 016 A3 | 11/1990 |
| EP | 0 397 424 A2 | 11/1990 |
| EP | 0 520 443 A2 | 12/1992 |
| EP | 0 255-338 A2 | 2/1998 |
| EP | 0 849 584 A2 | 6/1998 |
| EP | 1 266-607 A2 | 12/2002 |
| EP | 1 266-607 A3 | 12/2002 |
| EP | 1 369 688 A2 | 10/2003 |
| EP | 1 369 688 A3 | 10/2003 |
| EP | 1 360-934 A1 | 11/2003 |
| EP | 1 360-934 B1 | 11/2003 |
| EP | 1 486-766 A1 | 12/2004 |
| EP | 1 486-766 B1 | 12/2004 |
| EP | 1 529-489 A1 | 5/2005 |
| EP | 1 529-489 B1 | 5/2005 |
| EP | 1 769-735 A1 | 4/2007 |
| EP | 1 787 584 A1 | 5/2007 |
| EP | 1 987 766 A2 | 11/2008 |
| EP | 2 015 067 A1 | 1/2009 |
| JP | 63-305841 A | 12/1988 |
| JP | 3-63570 A | 3/1991 |
| JP | 03093189 A | 4/1991 |
| JP | 7-67861 A | 3/1995 |
| JP | 7-213925 A | 8/1995 |
| JP | 9-168530 A | 6/1997 |
| JP | 9-313465 A | 9/1997 |
| JP | 9-266889 A | 10/1997 |
| JP | 9-294737 A | 11/1997 |
| JP | 10-024028 A | 1/1998 |
| JP | 10-505258 A | 5/1998 |
| JP | 10-508518 A | 8/1998 |
| JP | 10-318970 A | 12/1998 |
| JP | 11-056822 A | 3/1999 |
| JP | 11-281779 A | 10/1999 |
| JP | 2000-116629 A | 4/2000 |
| JP | 2000-126161 A | 5/2000 |
| JP | 2000-168754 A | 6/2000 |
| JP | 2000-254111 A | 9/2000 |
| JP | 2001-159618 A | 6/2001 |
| JP | 2001-515203 A | 9/2001 |
| JP | 2001-305096 A | 10/2001 |
| JP | 2001-330581 A | 11/2001 |
| JP | 2002-502045 A | 1/2002 |
| JP | 2002-085384 A | 3/2002 |
| JP | 2002-514453 A | 5/2002 |
| JP | 2002-168862 A | 6/2002 |
| JP | 2003-507719 A | 2/2003 |
| JP | 2003-108679 A | 4/2003 |
| JP | 2003-180417 A2 | 7/2003 |
| JP | 2004-000598 A | 1/2004 |
| JP | 2004-500948 A | 1/2004 |
| JP | 2004-117339 A | 4/2004 |
| JP | 2004-202256 A | 7/2004 |
| JP | 2004-209266 A | 7/2004 |
| JP | 2004-519302 A | 7/2004 |
| JP | 2004-522500 A | 7/2004 |
| JP | 2004-528936 A | 9/2004 |
| JP | 2005-009238 A1 | 2/2005 |
| JP | 2005-503538 A | 2/2005 |
| JP | 2005-087613 A | 4/2005 |
| JP | 2006-512969 A | 4/2005 |
| JP | 3638958 B2 | 4/2005 |
| JP | 2005-525149 A | 8/2005 |
| JP | 2005-237938 A | 9/2005 |
| JP | 2005-525846 A | 9/2005 |
| JP | 2005-527254 A | 9/2005 |
| JP | 2006-506185 A | 2/2006 |
| JP | 2006-512974 A | 4/2006 |
| JP | 2006-516723 A | 7/2006 |
| JP | 2006-521555 A | 9/2006 |
| JP | 2006-527013 A | 11/2006 |
| JP | 2007-014381 A | 1/2007 |
| JP | 2007-054407 A | 3/2007 |
| JP | 2007-067698 A | 3/2007 |
| JP | 2007-136198 A | 6/2007 |
| JP | 2007-521031 A | 8/2007 |
| JP | 2007-311196 A | 11/2007 |
| JP | 2007-537804 A | 12/2007 |
| JP | 2008-125813 A | 6/2008 |
| WO | WO-86/05966 A1 | 10/1986 |
| WO | WO-88/00812 A1 | 2/1988 |
| WO | WO-88/07666 A1 | 10/1988 |
| WO | WO-91/14212 A1 | 9/1991 |
| WO | WO-94/13203 A1 | 6/1994 |
| WO | WO-95/10223 A2 | 4/1995 |
| WO | WO-95/10223 A3 | 4/1995 |
| WO | WO-96/04857 A1 | 2/1996 |
| WO | WO-96/07907 A1 | 3/1996 |
| WO | WO-96/14026 A1 | 5/1996 |
| WO | WO-96/25088 A1 | 8/1996 |
| WO | WO-97/04707 A1 | 2/1997 |
| WO | WO-97/15227 A1 | 5/1997 |
| WO | WO-97/29847 A1 | 8/1997 |
| WO | WO-97/30344 A1 | 8/1997 |
| WO | WO-97/41421 A1 | 11/1997 |
| WO | WO-97/42885 A1 | 11/1997 |
| WO | WO-97/42888 A1 | 11/1997 |
| WO | WO-97/43962 A1 | 11/1997 |
| WO | WO-98/00193 A1 | 1/1998 |
| WO | WO-98/31275 A1 | 7/1998 |
| WO | WO-98/35225 A1 | 8/1998 |
| WO | WO-99/12008 A1 | 3/1999 |
| WO | WO-99/23492 A1 | 5/1999 |
| WO | WO-99/44508 A1 | 9/1999 |
| WO | WO-99/56954 A1 | 11/1999 |
| WO | WO-99/58051 A1 | 11/1999 |
| WO | WO-99/62576 A1 | 12/1999 |
| WO | WO-00/09184 A1 | 2/2000 |
| WO | WO-00/13573 A1 | 3/2000 |
| WO | WO-00/14269 A1 | 3/2000 |
| WO | WO-00/14535 A1 | 3/2000 |
| WO | WO-00/18449 A2 | 4/2000 |
| WO | WO-00/18449 A3 | 4/2000 |
| WO | WO-00/19185 | 4/2000 |
| WO | WO-00/36400 A1 | 6/2000 |
| WO | WO-00/42422 A1 | 7/2000 |
| WO | WO-00/74763 A2 | 12/2000 |
| WO | WO-00/74763 A3 | 12/2000 |
| WO | WO-00/78208 A1 | 12/2000 |
| WO | WO-01/13795 A1 | 3/2001 |
| WO | WO-01/16575 A1 | 3/2001 |
| WO | WO-01/52727 A1 | 7/2001 |

(56) References Cited

FOREIGN PATENT DOCUMENTS

| | | |
|---|---|---|
| WO | WO-01/64105 A1 | 9/2001 |
| WO | WO-01/64105 C2 | 9/2001 |
| WO | WO-01/72220 A1 | 10/2001 |
| WO | WO-01/80728 A1 | 11/2001 |
| WO | WO-01/85233 A2 | 11/2001 |
| WO | WO-01/85233 A3 | 11/2001 |
| WO | WO-01/91634 A2 | 12/2001 |
| WO | WO-01/91634 A3 | 12/2001 |
| WO | WO-02/00101 A2 | 1/2002 |
| WO | WO-02/00101 A3 | 1/2002 |
| WO | WO-02/49507 A1 | 6/2002 |
| WO | WO-02/49509 A2 | 6/2002 |
| WO | WO-02/49509 A3 | 6/2002 |
| WO | WO-02/078533 A2 | 10/2002 |
| WO | WO-02/078533 A3 | 10/2002 |
| WO | WO-02/082052 A2 | 10/2002 |
| WO | WO-02/082052 A3 | 10/2002 |
| WO | WO-02/093144 A1 | 11/2002 |
| WO | WO-02/100251 A2 | 12/2002 |
| WO | WO-02/100251 A3 | 12/2002 |
| WO | WO-02/101359 A2 | 12/2002 |
| WO | WO-02/101359 A3 | 12/2002 |
| WO | WO-03/007819 A1 | 1/2003 |
| WO | WO-2003/030984 A1 | 4/2003 |
| WO | WO-2003/066128 A2 | 8/2003 |
| WO | WO-2003/066128 A3 | 8/2003 |
| WO | WO-2003/070099 A1 | 8/2003 |
| WO | WO-2003/071940 A1 | 9/2003 |
| WO | WO-2003/071940 C1 | 9/2003 |
| WO | WO-2004/045375 A2 | 6/2004 |
| WO | WO-2004/045375 A3 | 6/2004 |
| WO | WO-2004/062499 A1 | 7/2004 |
| WO | WO-2004/062500 A1 | 7/2004 |
| WO | WO-2004/062500 C1 | 7/2004 |
| WO | WO-2004/064636 A1 | 8/2004 |
| WO | WO-2004/085995 A2 | 10/2004 |
| WO | WO-2004/085995 A3 | 10/2004 |
| WO | WO-2004/091693 A2 | 10/2004 |
| WO | WO-2004/091693 A3 | 10/2004 |
| WO | WO-2004/105827 A2 | 12/2004 |
| WO | WO-2004/105827 A3 | 12/2004 |
| WO | WO-2005/006939 A2 | 1/2005 |
| WO | WO-2005/006939 A3 | 1/2005 |
| WO | WO-2005/009238 A1 | 2/2005 |
| WO | WO-2005/013824 A1 | 2/2005 |
| WO | WO-2005/018709 A2 | 3/2005 |
| WO | WO-2005/018709 A3 | 3/2005 |
| WO | WO-2005/018710 A2 | 3/2005 |
| WO | WO-2005/018710 A3 | 3/2005 |
| WO | WO-2005/084543 A1 | 9/2005 |
| WO | WO-2005/084546 A2 | 9/2005 |
| WO | WO-2005/084546 A3 | 9/2005 |
| WO | WO-2005/085995 A1 | 9/2005 |
| WO | WO-2005/112763 A1 | 12/2005 |
| WO | WO-2006/138226 A2 | 12/2006 |
| WO | WO-2006/138226 A3 | 12/2006 |
| WO | WO-2007/041062 A2 | 4/2007 |
| WO | WO-2007/041062 A3 | 4/2007 |
| WO | WO-2007/041063 A2 | 4/2007 |
| WO | WO-2007/041063 A3 | 4/2007 |
| WO | WO-2007/041244 A2 | 4/2007 |
| WO | WO-2007/041244 A3 | 4/2007 |
| WO | WO-2007/041287 A2 | 4/2007 |
| WO | WO-2007/041287 A3 | 4/2007 |
| WO | WO-2007/041355 A2 | 4/2007 |
| WO | WO-2007/041355 A3 | 4/2007 |
| WO | WO-2007/108519 A1 | 9/2007 |
| WO | WO-2007/112034 A2 | 10/2007 |
| WO | WO-2007/112034 A3 | 10/2007 |
| WO | WO-2008/027319 A2 | 3/2008 |
| WO | WO-2008/027319 A3 | 3/2008 |
| WO | WO-2008/062648 A1 | 5/2008 |
| WO | WO-2009/145920 A1 | 12/2009 |
| WO | WO-2009/148624 A1 | 12/2009 |
| WO | WO-2009/148626 A1 | 12/2009 |
| WO | WO-2011/065981 A1 | 6/2011 |
| WO | WO-2011/162823 A1 | 12/2011 |
| WO | WO-2013/020103 A1 | 2/2013 |
| WO | WO-2014/205412 A1 | 12/2014 |

OTHER PUBLICATIONS

ADA (Jan. 1994). "Self-Monitoring of Blood Glucose," Consensus Statement *Diabetes Care* 17(1):81-86.

Anonymous. (Sep. 30, 1993). "The Effect of Intensive Treatment of Diabetes on the Development and Progression of Long-Term Complications in Insulin-Dependent Diabetes Mellitus." *The New England Journal of Medicine* 329(14):977-986.

Anonymous. (Jun. 23, 1998). "Taking the "Ouch" Out of Needles: Arrays of "Microneedles" Offer New Techniques for Drug Delivery," *Science Daily,* located at <http:www.sciencedaily.com/releases/1998/06/980623045850.htm>, last visited Jan. 14, 2014, 3 pages.

Beregszàszi, M. et al. (Jul. 1997). "Nocturnal Hypoglycemia in Children and Adolescents with Insulin-Dependent Diabetes Mellitus: Prevalence and Risk Factors," *J. Pediatrics* 131(1 Pt. 1):27-33.

Brazzle, J. et al. Active Microneedles with Integrated Functionality, Solid-State Sensor and Actuator Workshop, Hilton Head Island, South Carolina, Jun. 4-8, 2000, Technical Digest, 199-202.

Burge, M.R., (Aug. 2001). "Lack of Compliance with Home Blood Glucose Monitoring Predicts Hospitalization in Diabetes", Diabetes Care 24(8): 1502-1503.

Chase, H.P. et al. (Feb. 2001). "Continuous Subcutaneous Glucose Monitoring in Children with Type 1 Diabetes," *Pediatrics* 107(2):222-226.

Clarke, W.L. et al. (Sep.-Oct. 1987). "Evaluating Clinical Accuracy of Systems for Self-Monitoring of Blood Glucose," *Diabetes Care* 10(5):622-628.

Clarke, W.L. et al. (1981). "Evaluation of a New Reflectance Photometer for Use in Home Blood Glucose Monitoring," *Diabetes Care* 4(5):547-550.

Collison, M.E. et al. (Sep. 1999). "Analytical Characterization of Electrochemical Biosensor Test Strips for Measurement of Glucose in Low-Volume Interstitial Fluid Samples," *Clinical Chemistry* 45(9):1665-1673.

Coster, S. et al. (2000). "Monitoring Blood Glucose Control in Diabetes Mellitus: A Systematic Review." *Health Technology Assessment* 4(12):1-93.

Cox, D.J. et al. (Jun. 1997). "Understanding Error Grid Analysis," *Diabetes Care* 20(6):911-912.

D'Arrigo, T.D. (Mar. 2000). "GlucoWatch Monitor Poised for Approval," *Diabetes Forecast,* 53(3):43-44.

Extended European Search Report dated Nov. 21, 2016, for EP Application No. 16 172 370.5, filed on Nov. 30, 2010, 9 pages.

Extended European Search Report dated Dec. 17, 2014, for EP Application No. 10 833 694.2, filed on Nov. 30, 2010, 11 pages.

Extended European Search Report dated Feb. 22, 2012, for EP Application No. EP 10 18 1155, filed Sep. 28, 2010, 6 pages.

Extended European Search Report dated Nov. 8, 2016, for EP Application No. 16 167 087.2, filed on Aug. 3, 2012, 7 pages.

Extended European Search Report dated Apr. 19, 2011, for EP Application No. 10 18 0848.3 filed Sep. 28, 2010, 5 pages.

Extended European Search Report dated Jan. 22, 2013, for EP Application No. 12182900.6, filed on Sep. 29, 2006, 6 pages.

Extended European Search Report dated Apr. 29, 2013 for EP Patent Application No. 12192620.8, filed on Nov. 14, 2012, 8 pages.

Extended European Search Report dated Jul. 18, 2013, for EP Application No. 06 772 943.4, filed on Jun. 13, 2006, 7 pages.

Extended European Search Report dated Feb. 2, 2016 for European Patent Application No. 15187274.4, filed on Sep. 29, 2015, 6 pages.

Feldman, B. et al. (2000). "FreeStyle™: A Small-Volume Electrochemical Glucose Sensor for Home Blood Glucose Testing," *Diabetes Technology and Therapeutics,* 2(2):221-229.

Final Office Action dated Jul. 9, 2008, for U.S. Appl. No. 11/529,613, filed Sep. 29, 2006, 19 pages.

Final Office Action dated Nov. 23, 2009, for U.S. Appl. No. 11/529,613, filed Sep. 29, 2006, 20 pages.

(56) References Cited

OTHER PUBLICATIONS

Final Office Action dated Jan. 21, 2011, for U.S. Appl. No. 11/529,613, filed Sep. 29, 2006, 7 pages.
Final Office Action dated Aug. 15, 2013 for U.S. Appl. No. 13/562,129, filed Jul. 30, 2012, 12 pages.
Final Office Action dated Apr. 13, 2016, for U.S. Appl. No. 13/669,366, filed Nov. 5, 2012, 31 pages.
Final Office Action dated Aug. 28, 2014, for U.S. Appl. No. 13/562,129, filed Jul. 30, 2012, 11 pages.
Final Office Action dated Dec. 26, 2014, for U.S. Appl. No. 13/669,366, filed Nov. 5, 2012, 9 pages.
Final Office Action dated Jan. 22, 2014, for U.S. Appl. No. 13/669,366, filed Nov. 5, 2012, 8 pages.
Final Office Action dated Jun. 30, 2010, for U.S. Appl. No. 11/529,612, filed Sep. 29, 2006, 11 pages.
Final Office Action dated May 30, 2007, for U.S. Appl. No. 11/125,107, filed May 10, 2005, 11 pages.
Final Office Action dated Nov. 1, 2010, for U.S. Appl. No. 11/311,667, filed Dec. 20, 2005, 9 pages.
Final Office Action dated Nov. 21, 2011, for U.S. Appl. No. 11/311,667, filed Dec. 20, 2005, 8 pages.
Final Office Action dated Jun. 11, 2010, for U.S. Appl. No. 11/529,614, filed Sep. 29, 2006, 16 pages.
Final Office Action dated Mar. 10, 2015, for U.S. Appl. No. 11/529,614, filed Sep. 29, 2006, 24 pages.
Final Office Action dated Oct. 15, 2009, for U.S. Appl. No. 11/239,122, filed Sep. 30, 2005, 13 pages.
Final Office Action dated Aug. 14, 2012, for U.S. Appl. No. 13/037,089, filed Feb. 28, 2011, 14 pages.
Final Office Action dated Sep. 23, 2013, for U.S. Appl. No. 13/037,089, filed Feb. 28, 2011, 14 pages.
Final Office Action dated Mar. 5, 2009, for U.S. Appl. No. 11/239,123, filed Sep. 30, 2005, 17 pages.
Final Office Action dated Mar. 3, 2011, for U.S. Appl. No. 11/239,123, filed Sep. 30, 2005, 25 pages.
Final Office Action dated Jan. 6, 2016, for U.S. Appl. No. 14/321,631, filed Jul. 1, 2014, 9 pages.
Hemmerich, K.J. et al. (Apr. 1995)."Guide to Engineering Thermoplastics," Medical Devices and Diagnostic Industry pp. 39-59.
INTEG. (2000). "LifeGuide™ Glucose Meter. No Lancets. No Blood," located at <http://www.integonline.com>, last visited May 1, 2000, 10 pages.
International Search Report dated Jan. 28, 2011, for PCT Application No. PCT/US2010/003063, filed on Nov. 30, 2010, 1 page.
International Search Report dated Dec. 3, 2004, for PCT Application No. PCT/US2004/08798, filed on Mar. 24, 2004, 3 pages.
International Search Report dated May 2, 2007, for PCT Application No. PCT/US2006/37923, filed on Sep. 9, 2006, 1 page.
International Search Report dated Aug. 16, 2007 for PCT Application No. PCT/US2006/038163, filed on Sep. 29, 2006, 1 page.
International Search Report dated Aug. 17, 2007 for PCT/US2006/38049, filed on Sep. 29, 2006, 1 page.
International Search Report dated Oct. 19, 2012 for PCT Application No. PCT/US2012/049629, filed on Aug. 3, 2012, 4 pages.
International Search Report dated Jan. 16, 2008, for PCT Application No. PCT/US2006/022840, filed on Jun. 13, 2006, 1 page.
International Search Report dated Aug. 20, 2007 for PCT Application No. PCT/US2006/37245, filed on Sep. 26, 2006, 1 page.
Ishii H. et al., (Aug. 2001). "Seasonal Variation of Glycemic Control in Type 2 Diabetic Patients", Diabetes Care 24(8):1503.
Johnson, R.N. et al. (Jan. 1998). "Accuracy of Devices Used for Self-Monitoring of Blood Glucose," *Annals of Clinical Biochemistry* 35(1):68-74.
Johnson, R.N. et al. (Jan. 1999). "Analytical Error of Home Glucose Monitors: A Comparison of 18 Systems," *Annals of Clinical Biochemistry* 36(1):72-79.
Johnson, R.N. et al. (2001). "Error Detection and Measurement In Glucose Monitors," *Clinica Chimica Acta* 307:61-67.
Kumetrix, Inc. (Dec. 1999). "Painless Blood Glucose Monitoring, Courtesy of the Mosquito," *Start-Up* pp. 27-28.
Lee, S-C. (Jun. 1999). "Light Scattering by Closely Spaced Parallel Cylinders Embedded in a Finite Dielectric Slab," *Journal of the Optical Society of America A* 16(6):1350-1361.
Mahler, R.J. et al. (1999). "Clinical Review 102, Type 2 Diabetes Melitus: Update on Diagnosis Pathophysiology, and Treatment," *The Journal of Clinical Endocrinology and Metabolism* 84(4):1165-1171.
Massey V. et al. (Aug. 1960). "Studies on the Reaction Mechanism of Lipoyl Dehydrogenase" Biochim. Biophys. Acta 48: 33-47.
McGarraugh, G. et al. (2001). "Physiological Influences on Off-Finger Glucose Testing," *Diabetes Technology & Therapeutics* 3(3):367-376.
McNichols, R.J. et al. (Jan. 2000). "Optical Glucose Sensing in Biological Fluids: An Overview," *Journal of Biomedical Optics,* 5(1):5-16.
Medline Plus. (Jun. 17, 2008). , Medical Encyclopedia, Monitor Blood Glucose-Series: Part 1-4, 6 pages.
Neeley, W.E. et al. (1981). "An Instrument for Digital Matrix Photometry," *Clinical Chemistry* 27(10):1665-1668.
Neeley, W.E. (1983). "Reflectance Digital Matrix Photometry," *Clinical Chemistry* 29(6):1038-1041.
Neeley, W.E. (1983). "Multilayer Film Analysis for Glucose in 1-µL Samples of Plasma," *Clinical Chemistry* 29(12):2103-2105.
Neeley, W.E. (1988). "A Reflectance Photometer with a Square Photodiode Array Detector for Use on Multilayer Dry-Film Slides," *Clinical Chemistry* 34(11):2367-2370.
Non-Final Office Action dated Dec. 12, 2007, for U.S. Appl. No. 11/529,613, filed Sep. 29, 2006, 13 pages.
Non-Final Office Action dated Apr. 28, 2009, for U.S. Appl. No. 11/529,613, filed Sep. 29, 2006, 21 pages.
Non-Final Office Action dated Jun. 4, 2010, for U.S. Appl. No. 11/529,613, filed Sep. 29, 2006, 23 pages.
Non-Final Office Action dated Mar. 23, 2012, for U.S. Appl. No. 13/197,592, filed Aug. 3, 2011, 7 pages.
Non-Final Office Action dated Mar. 23, 2012, for U.S. Appl. No. 13/197,603, filed Aug. 3, 2011, 6 pages.
Non-Final Office Action dated Nov. 26, 2012 for U.S. Appl. No. 13/562,129, filed Jul. 30, 2012, 9 pages.
Non-Final Office Action dated Apr. 8, 2015, for U.S. Appl. No. 13/566,886, filed Aug. 3, 2012, 11 pages.
Non-Final Office Action dated Mar. 19, 2009, for U.S. Appl. No. 11/239,122, filed Sep. 30, 2005, 15 pages.
Non-Final Office Action dated Sep. 1, 2010, for U.S. Appl. No. 11/239,122, filed Sep. 30, 2005, 15 pages.
Non-Final Office Action dated Apr. 12, 2011, for U.S. Appl. No. 11/311,667, filed Dec. 20, 2005, 7 pages.
Non-Final Office Action dated Aug. 5, 2014, for U.S. Appl. No. 13/669,366, filed Nov. 5, 2012, 8 pages.
Non-Final Office Action dated Dec. 5, 2014, for U.S. Appl. No. 13/562,129, filed Jul. 30, 2012, 7 pages.
Non-Final Office Action dated Jan. 12, 2009, for U.S. Appl. No. 11/529,612, filed Sep. 29, 2006, 9 pages.
Non-Final Office Action dated Jan. 21, 2011, for U.S. Appl. No. 11/529,612, filed Sep. 29, 2006, 9 pages.
Non-Final Office Action dated Jul. 13, 2010, for U.S. Appl. No. 12/222,724, filed Aug. 14, 2008, 11 pages.
Non-Final Office Action dated Jul. 31, 2015, for U.S. Appl. No. 13/669,366, filed Nov. 5, 2012, 16 pages.
Non-Final Office Action dated Mar. 21, 2014, for U.S. Appl. No. 13/562,129, filed Jul. 30, 2012, 12 pages.
Non-Final Office Action dated Mar. 25, 2011, for U.S. Appl. No. 12/222,724, filed Aug. 14, 2008, 13 pages.
Non-Final Office Action dated Mar. 5, 2010, for U.S. Appl. No. 11/311,667, filed Dec. 20, 2005, 8 pages.
Non-Final Office Action dated May 14, 2008, for U.S. Appl. No. 11/529,612, filed Sep. 29, 2006, 9 pages.
Non-Final Office Action dated May 16, 2013, for U.S. Appl. No. 13/669,366, filed Nov. 5, 2012, 8 pages.
Non-Final Office Action dated May 5, 2005, for U.S. Appl. No. 10/131,268, filed Apr. 23, 2002, 8 pages.
Non-Final Office Action dated Nov. 2, 2006, for U.S. Appl. No. 11/125,107, filed May 10, 2005, 10 pages.

(56) References Cited

OTHER PUBLICATIONS

Non-Final Office Action dated Oct. 14, 2009, for U.S. Appl. No. 11/529,612, filed Sep. 29, 2006, 10 pages.
Non-Final Office Action dated Oct. 3, 2008, for U.S. Appl. No. 10/722,074, filed Nov. 24, 2003, 10 pages.
Non-Final Office Action dated Dec. 17, 2015, for U.S. Appl. No. 11/529,614, filed Sep. 29, 2006, 6 pages.
Non-Final Office Action dated Dec. 2, 2004, for U.S. Appl. No. 10/347,620, filed Jan. 22, 2003, 8 pages.
Non-Final Office Action dated Jan. 27, 2009, for U.S. Appl. No. 11/529,614, filed Sep. 29, 2006, 17 pages.
Non-Final Office Action dated Jan. 6, 2014, for U.S. Appl. No. 11/529,614, filed Sep. 29, 2006, 12 pages.
Non-Final Office Action dated Jun. 21, 2013, for U.S. Appl. No. 13/752,261, filed Jan. 28, 2013, 12 pages.
Non-Final Office Action dated Jun. 6, 2008, for U.S. Appl. No. 11/529,614, filed Sep. 29, 2006, 17 pages.
Non-Final Office Action dated Oct. 9, 2014, for U.S. Appl. No. 14/446,262, filed Jul. 29, 2014, 15 pages.
Non-Final Office Action dated Sep. 29, 2004, for U.S. Appl. No. 10/394,230, filed Mar. 24, 2003, 10 pages.
Non-Final Office Action dated Sep. 13, 2011, for U.S. Appl. No. 13/037,089, filed Feb. 28, 2011, 14 pages.
Non-Final Office Action dated Feb. 28, 2013, for U.S. Appl. No. 13/037,089, filed Feb. 28, 2011, 12 pages.
Non-Final Office Action dated Apr. 10, 2014, for U.S. Appl. No. 13/037,089, filed Feb. 28, 2011, 14 pages.
Non-Final Office Action dated May 29, 2015, for U.S. Appl. No. 14/614,177, filed Feb. 4, 2015, 13 pages.
Non-Final Office Action dated Nov. 1, 2007, for U.S. Appl. No. 11/239,123, filed Sep. 30, 2005, 15 pages.
Non-Final Office Action dated Apr. 15, 2010, for U.S. Appl. No. 11/239,123, filed Sep. 30, 2005, 19 pages.
Non-Final Office Action dated Sep. 19, 2013, for U.S. Appl. No. 11/239,123, filed Sep. 30, 2005, 24 pages.
Non-Final Office Action dated Aug. 8, 2014, for U.S. Appl. No. 14/321,631, filed Jul. 1, 2014, 11 pages.
Notice of Allowance dated Apr. 3, 2014, for U.S. Appl. No. 11/239,123, filed Sep. 30, 2005, 6 pages.
Notice of Allowance dated Apr. 18, 2012, for U.S. Appl. No. 11/529,612, filed Sep. 29, 2006, 8 pages.
Notice of Allowance dated Apr. 19, 2010, for U.S. Appl. No. 29/338,117, filed Jun. 4, 2009, 4 pages.
Notice of Allowance dated Aug. 3, 2012, for U.S. Appl. No. 11/529,612, filed Sep. 29, 2006, 5 pages.
Notice of Allowance dated Jan. 14, 2010, for U.S. Appl. No. 29/338,117, filed Jun. 4, 2009, 4 pages.
Notice of Allowance dated Jun. 29, 2012, for U.S. Appl. No. 11/311,667, filed Dec. 20, 2005, 5 pages.
Notice of Allowance dated Mar. 14, 2012, for U.S. Appl. No. 12/222,724, filed Aug. 14, 2008, 7 pages.
Notice of Allowance dated Mar. 31, 2005, for U.S. Appl. No. 10/394,230, filed Mar. 24, 2003, 10 pages.
Notice of Allowance dated May 15, 2008, for U.S. Appl. No. 11/125,107, filed May 10, 2005, 7 pages.
Notice of Allowance dated May 18, 2009, for U.S. Appl. No. 29/300,934, filed May 30, 2008, 4 pages.
Notice of Allowance dated May 28, 2009, for U.S. Appl. No. 29/300,933, filed May 30, 2008, 6 pages.
Notice of Allowance dated Nov. 23, 2011, for U.S. Appl. No. 12/222,724, filed Aug. 14, 2008, 7 pages.
Notice of Allowance dated Nov. 27, 2012, for U.S. Appl. No. 11/529,612, filed Sep. 29, 2006, 5 pages.
Notice of Allowance dated Nov. 29, 2005, for U.S. Appl. No. 10/131,268, filed Apr. 23, 2002, 6 pages.
Notice of Allowance dated Oct. 12, 2011, for U.S. Appl. No. 11/529,612, filed Sep. 29, 2006, 8 pages.
Notice of Allowance dated May 3, 2011, for U.S. Appl. No. 11/529,613, filed Sep. 29, 2006, 12 pages.
Notice of Allowance dated Mar. 27, 2015, for U.S. Appl. No. 13/562,129, filed Jul. 30, 2012, 7 pages.
Notice of Allowance dated Feb. 23, 2015, for U.S. Appl. No. 14/446,262, filed Jul. 29, 2014, 8 pages.
Notice of Allowance dated Feb. 5, 2014, for U.S. Appl. No. 13/752,261, filed Jan. 28, 2013, 9 pages.
Notice of Allowance dated Jun. 15, 2009, for U.S. Appl. No. 10/722,074, filed Nov. 24, 2003, 6 pages.
Notice of Allowance dated Mar. 2, 2016, for U.S. Appl. No. 11/529,614, filed Sep. 29, 2006, 12 pages.
Notice of Allowance dated Mar. 28, 2005, for U.S. Appl. No. 10/347,620, filed Jan. 22, 2003, 6 pages.
Notice of Allowance dated Sep. 18, 2014, for U.S. Appl. No. 13/037,089, filed Feb. 28, 2011, 9 pages.
Notice of Allowance dated Feb. 16, 2016, for U.S. Appl. No. 14/614,177, filed Feb. 4, 2015, 7 pages.
Otto, E. et al. (2000). "An Intelligent Diabetes Software Prototype: Predicting Blood Glucose Levels and Recommending Regimen Changes," *Diabetes Technology and Therapeutics* 2(4):569-576.
Pfohl, M. et al. (2000). "Spot Glucose Measurement in Epidermal Interstitial Fluid—An Alternative to Capillary Blood Glucose Estimation," *Experimental and Clinical Endocrinology & Diabetes* 108(1):1-4.
Princen, H.M. (May 1969). "Capillary Phenomena in Assemblies of Parallel Cylinders, I. Capillary Rise Between Two Cylinders," *Journal of Colloid and Interface Science* 30(1):69-75.
Princen, H.M. (Jul. 1969). "Capillary Phenomena in Assemblies of Parallel Cylinders, II. Capillary Rise in Systems with More Than Two Cylinders," *Journal of Colloid and Interface Science* 30(3):359-371.
Rebrin, K. et al. (Sep. 1999). "Subcutaneous Glucose Predicts Plasma Glucose Independent of Insulin: Implications for Continuous Monitoring," *American Journal of Physiology* 277(3):E561-E571.
Rosen, S. (1999). "Road to New-Age Glucose Monitoring Still Rocky," *Diagnostic Insight*, pp. 4-5, 12-13, 16.
Smart, W.H. et al. (2000). "The Use of Silicon Microfabrication Technology in Painless Glucose Monitoring," *Diabetes Technology & Therapeutics* 2(4):549-559.
Spielman, A. et al. (2001). *Mosquito: A Natural History of Our Most Persistent and Deadly Foe*, First Edition, Hyperion, New York, NY, 3 pages. (Table of Contents Only).
Sonntag, O. (1993). Ektachem. Dry Chemistry, Analysis With Carrier-Bound Reagents, Elsevier Science Publishers. 57 pages.
Straub F.B. (Mar. 1939). "Isolation and Properties of a flavoprotien from Heart Muscle Tissue", Biochemical Journal 33: 787-792.
Svedman, C. et al. (Apr. 1999). "Skin Mini-Erosion Technique for Monitoring Metabolites in Interstitial Fluid: Its Feasibility Demonstrated by OGTT Results in Diabetic and Non-Diabetic Subjects," *Scand. J. Clin. Lab. Invest.* 59(2):115-123.
Tietz, N.W. (1986). Textbook of Clinical Chemistry, W.B. Saunders Company, pp. 1533 and 1556.
Trinder, P. (1969). "Determination of Glucose in Blood Using Glucose Oxidase with an Alternate Oxygen Acceptor," *Annals of Clinical Biochemistry* 6:24-28.
U.S. Precision Lens, Inc. (1983).The Handbook of Plastic Optics.
Wikipedia (2016). "Capillary action," 7 pages.
Written Opinion dated Jan. 28, 2011, for PCT Application No. PCT/US2010/003063, filed on Nov. 30, 2010, 6 pages.
Written Opinion dated Dec. 3, 2004, for PCT Application No. PCT/US2004/08798, filed on Mar. 24, 2004, 4 pages.
Written Opinion dated May 2, 2007, for PCT Application No. PCT/US2006/37923, filed on Sep. 9, 2006, 5 pages.
Written Opinion dated Aug. 17, 2007 for PCT/US2006/38049, filed on Sep. 29, 2006, 6 pages.
Written Opinion dated Aug. 20, 2007 for PCT Application No. PCT/US2006/37245, filed on Sep. 26, 2006, 7 pages.
Written Opinion dated Aug. 16, 2007 for PCT Application No. PCT/US2006/038163, filed on Sep. 29, 2006, 4 pages.
Written Opinion dated Oct. 19, 2012 for PCT Application No. PCT/US2012/049629, filed on Aug. 3, 2012, 7 pages.

(56) References Cited

OTHER PUBLICATIONS

Written Opinion of the International Searching Authority dated Jan. 16, 2008, for PCT Application No. PCT/US2006/022840, filed on Jun. 13, 2006, 3 pages.
Yum, S. I. et al. (Nov. 1, 1999). "Capillary Blood Sampling for Self-Monitoring of Blood Glucose," *Diabetes Technology & Therapeutics,* 1(1):29-37.
Extended European Search Report dated Nov. 8, 2016 from the European Patent Office for Application No. 16167087.2, filed Aug. 3, 2012, 6 pages.
Non-Final Office Action dated Dec. 16, 2016, for U.S. Appl. No. 13/566,886, filed Aug. 3, 2012, 11 pages.
Non-Final Office Action dated Mar. 20, 2017, by the United States Patent and Trademark Office for U.S. Appl. No. 15/191,434, filed Jun. 23, 2016, 20 pages.
Non-Final Office Action dated Mar. 21, 2017, for U.S. Appl. No. 15/177,041, filed Jun. 8, 2016, 11 pages.
Non-Final Office Action dated Jun. 20, 2017, for U.S. Appl. No. 15/191,434, filed Jun. 23, 2016, 20 pages.

* cited by examiner

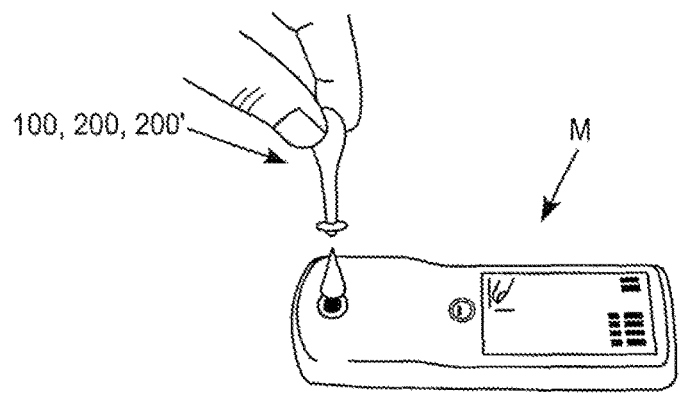
FIG. 28A
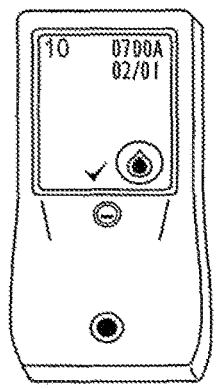
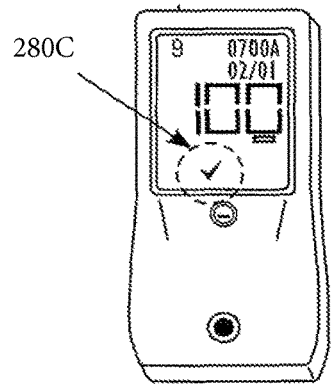
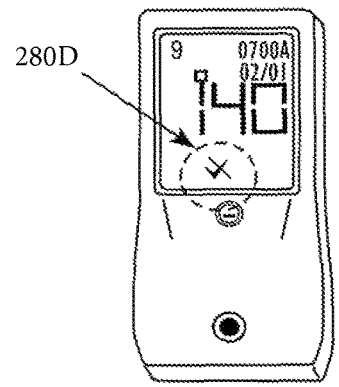
FIG. 28B     FIG. 28C     FIG. 28D

CALIBRATION MATERIAL DELIVERY DEVICES AND METHODS

CROSS-REFERENCE TO RELATED APPLICATIONS

The present application is a continuation of U.S. patent application Ser. No. 12/957,215, filed Nov. 30, 2010, which issued as U.S. Pat. No. 8,919,605 on Dec. 30, 2014, the disclosure of which is herein incorporated by reference in its entirety. U.S. patent application Ser. No. 12/957,215 claims priority to U.S. Patent Application No. 61/358,791, filed Jun. 25, 2010, and U.S. Patent Application No. 61/265,247, filed Nov. 30, 2009.

FIELD

The inventions described herein relates to devices and methods of delivering calibration or control information to a device, such as an analyte monitor.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

Currently, analyte monitoring devices, such as blood glucose monitors, include a method of executing a "control fluid" test to determine if the device is functioning according to the manufacturer's expectations. Typically, users complete a "control" test by dispensing a variable amount of fluid onto a test strip from a vial packaged with the test kit. This vial contains a fluid within a known analyte concentration. After the users dispense the fluid onto the test strip the analyte monitor assumes the fluid is a body fluid and provides a result as usual. The device and/or the user can compare, the concentration of target analyte, measured by the device with the known concentration contained in the control solution as a measure of the accuracy of the monitoring device.

Current systems require the user to dispense the calibration fluid from a vial containing several doses of calibration fluid. When dispensing the fluid the user must take care not to spill the fluid on the device, or on the testing surface. Completing a control test also requires that users have the dexterity to deliver a small droplet of control solution from a vial onto the test strip; this is especially difficult when diseases such as diabetes affect the patient's vision and tactile sensation.

A typical calibration or control test requires the following steps:
1. users fire their control vial
2. ensure that the control solution is still within its expiration limits
3. find a test strip
4. insert the test strip into the device or meter
5. place the device into "control test mode" (if applicable)
6. shake the bottle of solution
7. open the control vial (using two-hands)
8. carefully squeeze out enough control solution onto the test strip or the finger, taking care not to damage the analyte monitor by dispensing too much fluid
9. accurately deliver the control solution to the analyte monitor
10. compare the result of the control test versus the stated control range which may or may not be listed on the control vial
11. mark the control test in their logbook so that health care professionals can remove this test from the users monthly averages if so desired.

Currently many users of analyte monitors find executing a control test to be a burdensome experience that they often ignore. By ignoring the control test users often will acquire erroneous information from their monitors, and this information may then be used to adjust drug treatments. The use of inaccurate information can lead to serious consequences, such as hypoglycemia in diabetes patients from a dosage of insulin that is too high.

While certain aspects of conventional technologies have been discussed to facilitate disclosure of the invention, Applicants in no way disclaim these technical aspects, and it is contemplated that the claimed invention may encompass or include one or more of the conventional technical aspects discussed herein.

SUMMARY

As used herein, "body fluid" encompasses whole blood, interstitial fluid, and mixtures thereof.

As used herein "integrated device" or "integrated meter" means a device or meter that includes all components necessary to perform sampling of body fluid, transport of body fluid, quantification of an analyte, and display of the amount of analyte contained in the sample of body fluid. Exemplary integrated meters are described in: U.S. Pat. Nos. 8,540,675 and 7,004,928; U.S. Patent Application Publication Nos. US 2008/0077048, US 2007/0179404, US 2007/0083131, US 2007/0179405, US 2007/0078358, and US 2007/0078313. The entire contents of each of the above-listed documents are incorporated herein by reference.

As used herein, "control material" means a material having a known and/or predetermined quantity or concentration of at least one, and possibly a plurality of, analyte(s) contained therein. The material can possess any suitable form. For example, the control material, can be in the form of a liquid, a solid, a granular solid, a gas, a gel, a solution, a suspension, or any combination thereof. The analyte can comprise any suitable analyte. For example, the analyte can comprise one, or more of: glucose, bilirubin alcohol, controlled substances, toxins, hormones, and/or proteins.

It is to be understood that reference herein to first, second, third and fourth components (etc.) does not limit the present invention to embodiments where each of these components is physically separable from one another. For example, a single physical element of the invention may perform the functions of more than one of the claimed first, second, third or fourth components. Conversely, a plurality of separate physical elements working together may perform the functions of one of the claimed first, second, third or fourth components. Similarly, reference to first, second (etc.) method steps does not limit the invention to only separate steps. According to the invention, a single method step may satisfy multiple steps described herein. Conversely, a plurality of method steps could, in combination, constitute a single method step recited herein. In addition, the steps of the method are not necessarily limited to the order in which they are described or claimed herein.

It should also be understood that references herein to "the invention," or similar language, is used to enhance readability and for convenience only, and should not be interpreted as a limitation on what is contemplated and comprehended by this disclosure and the appended claims. Instead "the invention" is intended to be interpreted as encompassing the full scope of what is claimed, regardless of the characterizations of the specific exemplary and non-limiting embodiments described in the specification.

The present invention may address one or more of the problems and deficiencies of the prior art discussed above. However, it is contemplated that the invention may prove useful in addressing other problems and deficiencies, or provides benefits and advantages, in a number of technical areas. Therefore the claimed invention should not necessarily be construed as being limited to addressing any of the particular problems or deficiencies discussed herein.

The invention can be useful with any device but is particularly applicable to analyte monitors used in a home or clinical setting such as glucose monitors. The invention provides users of such monitors with a device that allows them to quickly and easily deliver one or more doses of calibration or control information to one or more devices, such as an analyte monitor. The invention also provides for mechanisms and methods that can automatically differentiate a calibration test from a typical test. This invention is aimed at devices requiring calibration or the ability to execute a control test. For example, in the case of analyte monitors where an analyte of a known concentration is delivered to the analyte monitor to ensure that it is functioning properly. According to the principles of the present invention, a typical user can easily and quickly execute a proper calibration test to ensure device functionality without assistance from a trained health care professional. Alternatively, the present invention can also be utilized by medical professionals in a clinical setting.

The invention can be used with an integrated device or integrated meter of the type defined above. However, the invention is not limited to use with fully integrated meters, and benefits can also be attained by use with conventional (non-integrated) meters and other diagnostic devices where collection of accurate data and analysis of data is important.

The invention can provide a device containing a single dosage, or multiple doses of control material in a convenient easy-to-use package. The control material can be contained within an applicator that is large enough for easy handling and sealed according to a number of alternative ways so that the risk of spillage or damage to the analyte monitor is greatly reduced.

This device simplifies a control test and encourages users to perform a control test more often so that any problems with their analyte monitors can be found more quickly.

The invention can provide for use of one or more dosage(s) of a predefined volume of control material, thereby ensuring more accurate data by allowing users to deliver the required amount of control solution, unlike previous methods in which it is quite possible that users could deliver too much or too little control solution. As previously mentioned, by sealing each dosage individually the viability of the control sample can be enhanced and users are less likely to use expired control material. The accuracy of the average data stored within the analyte monitor can also be increased by automatically marking or differentiating a control test from a normal or actual test so that the control test value can not impact the averages of normal analyte testing (weekly, monthly, etc) stored within the unit.

According to certain aspects, the invention provides mechanisms and methods that can determine automatically if the sampled material is body fluid or control material without the users intervention. Also, the individual packaging of each control test ensures that each solution dosage will remain enclosed in a protective environment and allows for an extended expiration date.

According to a first aspect, the present invention provides a device comprising: a first portion configured to be grasped by the hand of the user; and a second portion defining a reservoir containing a first control material, wherein the control material comprises a target analyte of a known or predetermined concentration.

According to another aspect, the present invention provides in combination, an integrated meter comprising a housing with an opening formed therein, and the device as described above, the second portion comprising a body and a flange shaped and configured to be received by the integrated meter.

According to an additional aspect, the present invention provides a method of conveying a control material to an analyte monitor, the method comprising: (i) providing a dispenser comprising a first portion configured to be grasped by the hand of the user, and a second portion defining a reservoir having a frangible seal thereon, the reservoir containing a control material, wherein the control material contains a target analyte in a known and/or predetermined concentration; (ii) breaking the frangible seal; and (iii) conveying the control material to a location for analysis by the analyte monitor.

According to another aspect, the present invention provides a method of verifying the accuracy of the operation of an analyte monitoring device using a control material having a known and/or predetermined concentration of at least one analyte, the method comprising: providing a single or multi-test cartridge having information associated therewith defining an acceptable range of measured analyte concentration values for the control material; associating the single or multi-test cartridge with the device; reading the information off the single or multi-test cartridge; introducing a control material to the single or multi-test cartridge; the device automatically determining the presence of a control material; analyzing the control material to measure the concentration of analyte contained therein; and comparing the measured concentration with the control information to determine if the measured concentration corresponds to the acceptable range of concentration values obtained from the information.

BRIEF DESCRIPTION OF THE DRAWING FIGURES

The following description of exemplary embodiments can be read in connection with the accompanying drawings in which like numerals designate like elements and in which:

FIGS. 28A-28D illustrate a method and possible uses of a device according to further alternative embodiments of the present invention.

DETAILED DESCRIPTION

In general terms this invention describes a device that allows a user to deliver a one or more doses of control material, such as a control fluid or control solution, to one or more devices such as a meter or monitor, for example, an integrated blood glucose monitor previously described herein. The method of and apparatus for delivery of the control solution can take many forms, such as a prepackaged "blister" of control solution or a "wand," with a known predetermined volume of control solution available for delivery to the analyte monitor. Exemplary, non-limiting embodiments of the present invention are illustrated in Figures which follow.

As illustrated in FIGS. 1-4, a device 10 constructed according to a first illustrated embodiment comprises two portions; a first portion 12 and a second portion 14. The first portion 12 serves primarily as a handle for manipulation of the device 10 by a user. Thus, the first portion 12 can be provided with any suitable form which provides the desired functionality. Therefore, it should be evident that the form of the first portion 12 is not limited to the illustrated embodiment. According to the non-limiting illustrated embodiment, the first portion 12 is in the form of an elongated cylindrical body.

Figure 1:
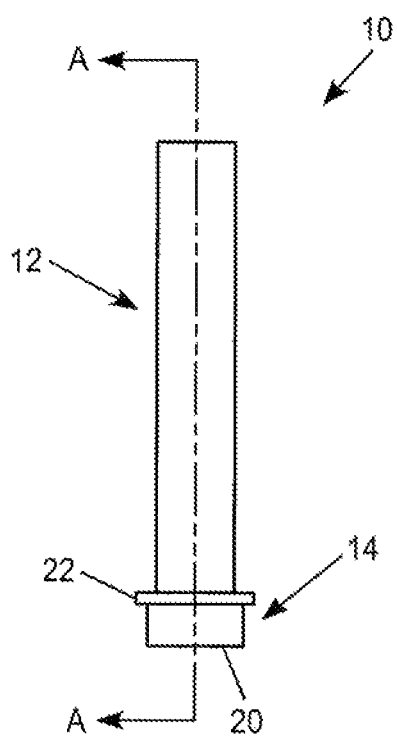
FIG. 1 is a side view of a device formed according to one embodiment of the present invention.
Figure 2:
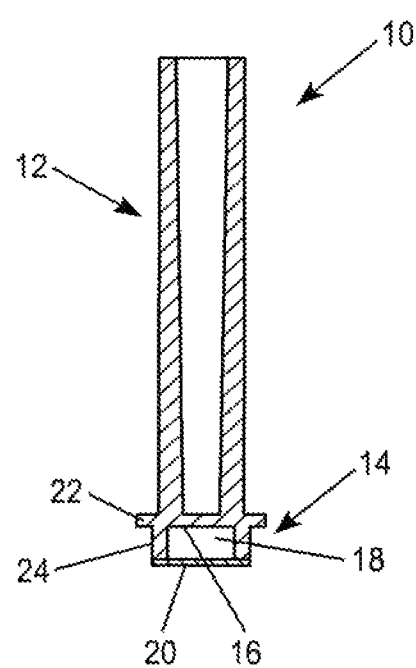
FIG. 2 is a sectional view taken at line A-A of FIG. 1.
Figure 3:
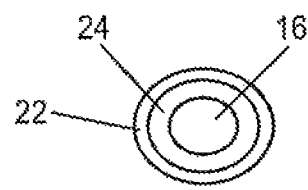
FIG. 3 is a bottom view of the device of FIG. 1.
Figure 4:
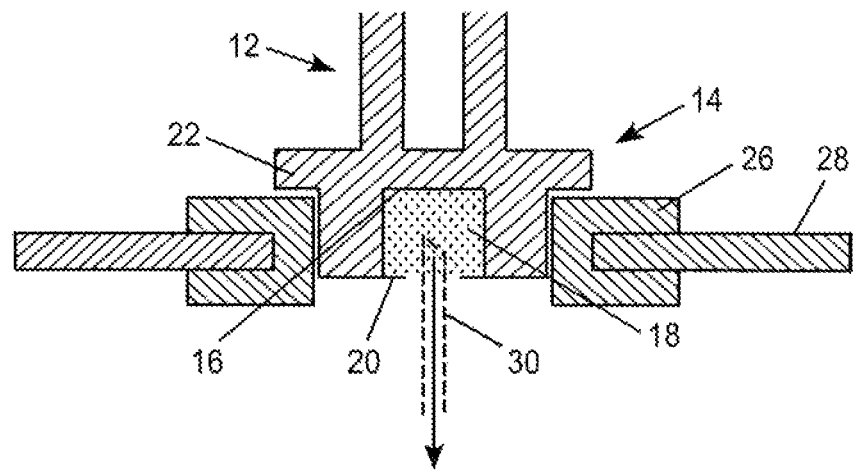
FIG. 4 is a schematic illustration of a device and a possible implementation, use or method involving the device, according to further alternative embodiments.
Figure 5:
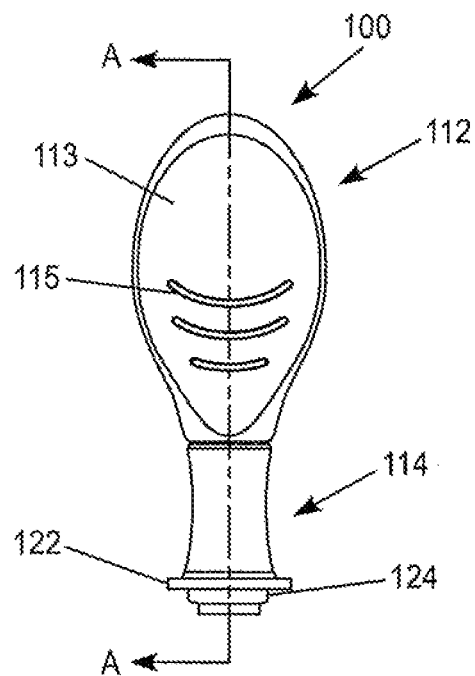
FIG. 5 is a side view of a device formed according to an additional alternative embodiment of the present invention.

The second portion 14 provides a mechanism for carrying a control or calibration material, as well as optionally mating with a meter or monitor (see, e.g. FIG. 4). Thus, the second portion 14 can have any suitable form that provides this functionality. According to the nonlimiting illustrated embodiment, the second portion 14 defines a reservoir 18. The reservoir 16 can have any suitable form, and is not limited to the form shown in the illustrated embodiment. The reservoir contains a control material. Any suitable control material can be utilized. The control material comprises a target analyte, such as glucose, in a known and/or predetermined concentration. Optionally, the control material may contain a plurality of target analytes. According to one alternative embodiment, the control material is in the form of a control liquid or solution. According to a further alternative embodiment, the control material is in the form of a liquid or solution that is carried by an absorbent or porous material, such as a sponge-like material. Thus, according to the one optional embodiment, the control material 18 is in the form of an absorbent or porous material having a control liquid, suspension or solution absorbed therein.

The reservoir 16 containing the control material 1 can be provided with a closure or seal 20. The closure or seal 20 acts to contain the control material 18 within the reservoir 16, and to prevent contamination by shielding the control material 18 from the environment. The closure or seal 20 can be provided in any suitable form, and can be constructed of any suitable material. According to one non-limiting example, the closure or seal 20 can be in the form of a thin, frangible, closure, such as a metallic foil.

As noted above, according to one optional embodiment, the second portion 14 serves to mate with an analyte monitor such that the control material 18 be dispensed. Thus, the second portion can be provided with a shape and size that renders it suitable for mating with a meter or monitor. It should be evident that the construction of the particular device with which the second portion 14 will mate can influence both the size and shape of the second portion 14. According to the nonlimiting illustrated example, the second portion 14 comprises a flanged 22 cylindrical body 24, as perhaps best seen in FIG. 3, which is dimensioned to mate with an opening formed in an analyte monitor, as best illustrated in FIG. 4. Thus, according to one possible implementation or embodiment of the present invention, an opening is formed in an analyte monitor by a flexible footprint or interface device 26 which is mounted to the housing 28 of the meter or monitor. The body 24 of the second portion 14 of the device 10 is inserted into the opening to a desired depth, which is controlled or defined by the location of the flange 22. According to one non-limiting example, the analyte monitor includes a piercing element, or hollow needle, 30 which can be actuated such that it breaks the seal 20 and comes into fluid communication with the control material 18. The hollow piercing element 30 then transports the control material 18 into the analyte monitor, as indicated by the arrow appearing in FIG. 4, wherein the monitor includes an appropriate mechanism for analyzing the control material to measure the concentration of the target analyte(s)

contained therein. Such mechanisms may include electrochemical or calorimetric analysis, as described in connection with the description of the integrated meters previously referenced herein.

A device constructed according to further alternative embodiments of the present invention is depicted in FIGS. 5-8. The device has a construction and functionality which is similar to that of the previously described embodiments. Therefore, where a feature of the alternative embodiments finds a corresponding feature with the previously described embodiments, they have been given similar reference numeral (e.g., 12 and 112). Therefore, reference is made to the previously described embodiments far a full description of these corresponding features.

As illustrated in FIGS. 5-8, the first portion 112 of the device 100 is provided with a configuration which facilitates handling by a user. This is particularly important when the device 100 is intended for use with blood glucose monitors. This is because people with diabetes can lack tactile dexterity. Thus, the first portion 112 of the device 100 can be provided with any suitable form which facilitates grasp by a user.

Figure 6:
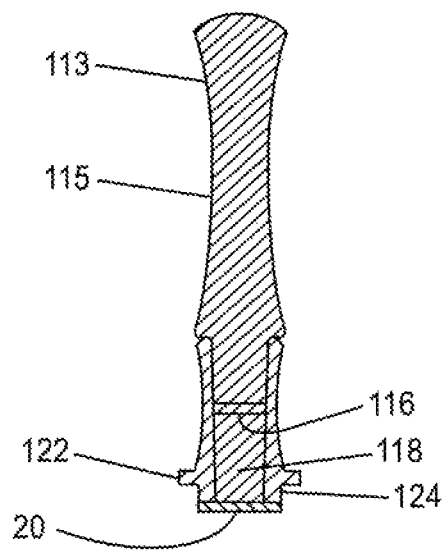
FIG. 6 is a sectional view taken at line A-A of FIG. 5.
Figure 7:
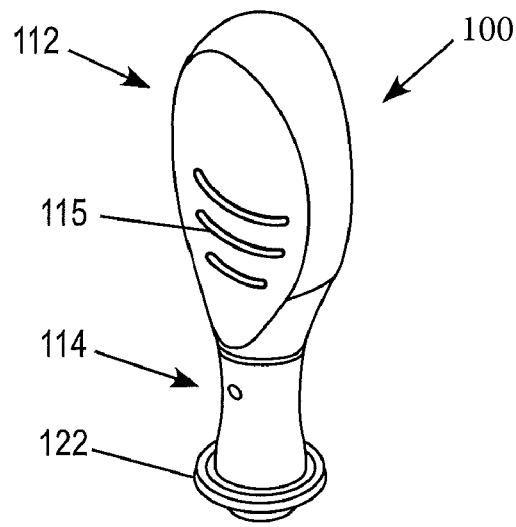
FIG. 7 is a perspective view of the device of FIG. 5.
Figure 8:
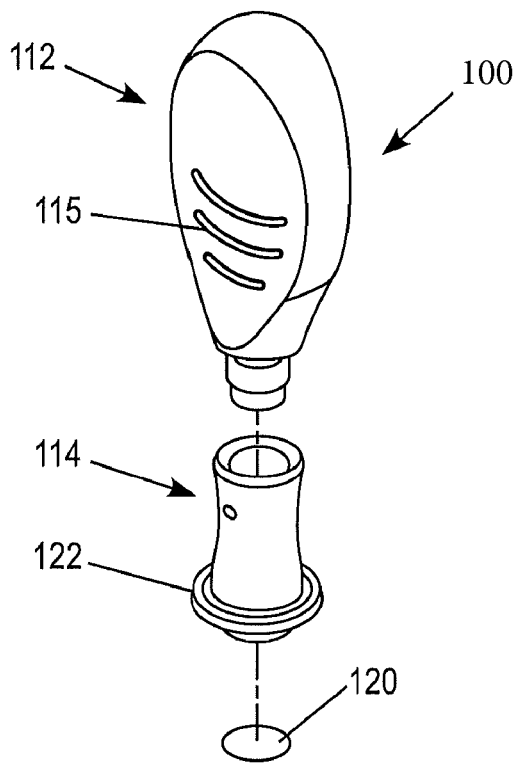
FIG. 8 is an exploded perspective view of the device of FIG. 5.
Figure 9:
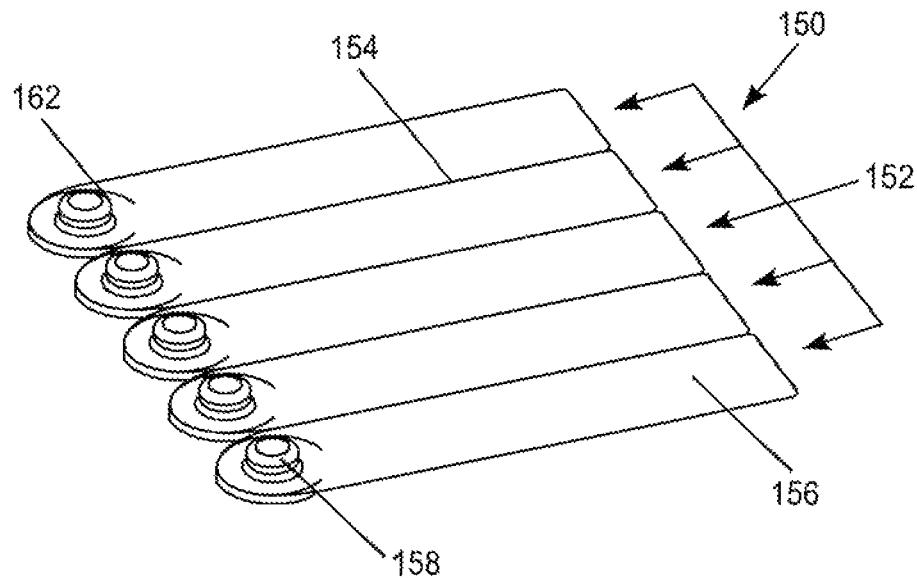
FIG. 9 is a perspective view of a device formed according to another embodiment of the present invention.
Figure 10:
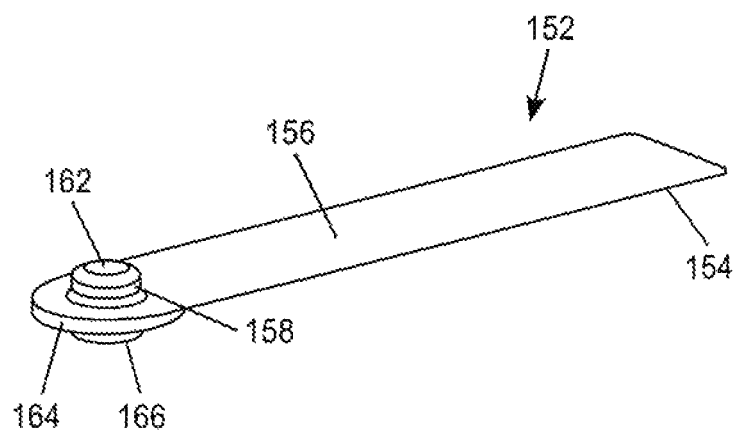
FIG. 10 is a perspective view of one of the individual devices of FIG. 9.
Figure 11:
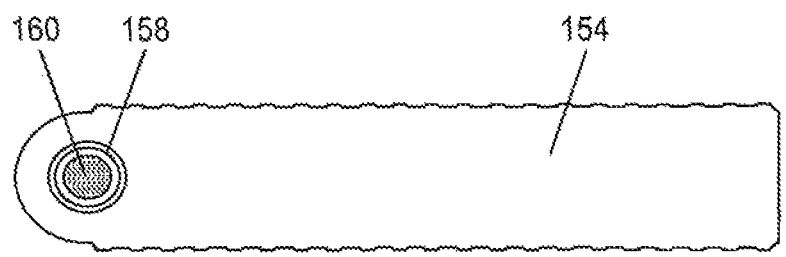
FIG. 11 is a top view of one of the individual devices of FIG. 9.
Figure 12:
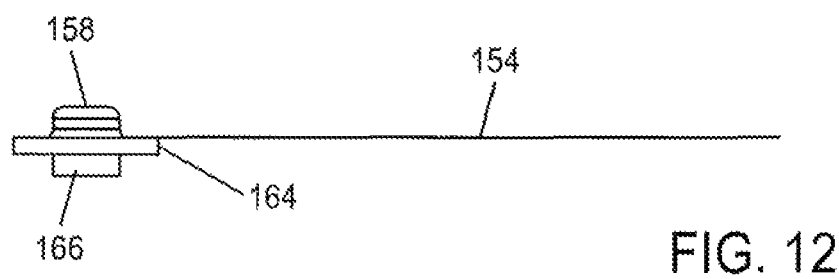
FIG. 12 is a side view of one of the individual devices of FIG. 9.
Figure 13:
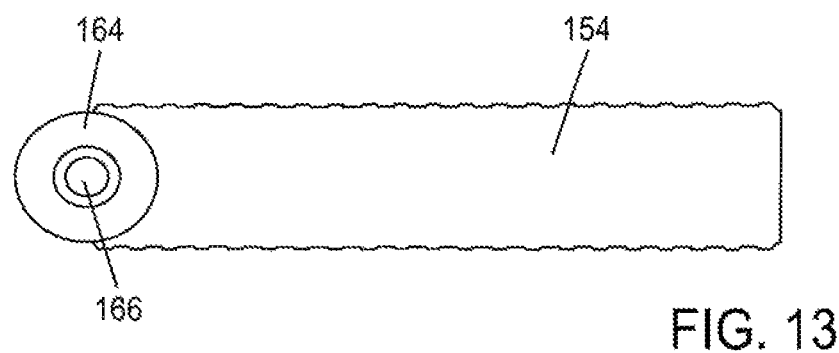
FIG. 13 is a bottom view of one of the individual devices of FIG. 9.
Figure 14:
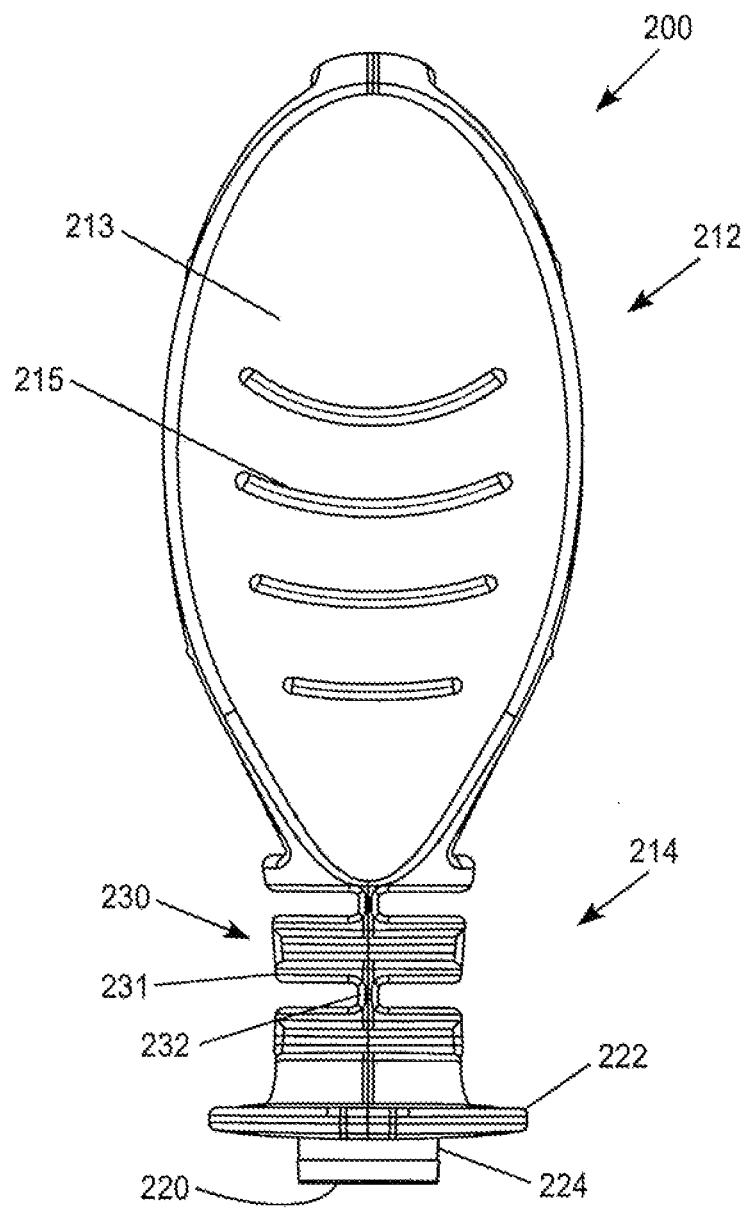
FIG. 14 is a side view of a device formed according to a further embodiment of the invention.

According to the illustrated embodiment the first portion 112 comprises a flattened relatively wide paddle-like shape. The paddle-like shape includes facing surfaces 113 which are contoured in an hourglass type manner such that the second portion 112 is provided with a cross-section that is relatively thin toward the middle, and wider towards its ends (FIG. 6). The second portion 112 may optionally be provided with a feature that reduces slippage. For example, according to the nonlimiting illustrated embodiment, the second portion 112 is provided with a series of raised projections or ribs 115. Alternative features, such as a high friction surface coating or material disposed on all or a portion of surfaces 113 and/or ribs 115 may also be provided.

The second portion 114 of the device 100 defines a reservoir 116, which houses a control material 118, which can take any suitable form, such as that described in connection with the previous embodiments. The reservoir 116 can be sealed by a corresponding closure or seal 120. The second portion 114 further comprises a flanged 122 body 124, configured in a manner similar to that of the previously described embodiment.

In the embodiments depicted in FIGS. 5-8, the first portion 112 in the second portion 114 are formed as separate components which are assembled together and secured in any suitable fashion, such as by adhesive or a fastener. However, it should be understood that the invention is not so limited. Namely, the device 100 can have an integral or single-piece monolithic construction.

It should be evident that the device 100 has a configuration such that it can be utilized in a manner similar to that of the previous embodiment, as depicted in FIG. 4 herein.

The device of the present invention, and components thereof, care be made of any suitable material, such as, metal, wood, plastic, etc. In a preferred embodiment, the device can be made of an injection molded plastic material to simplify production and reduce costs. Similarly, in one optional embodiment, a control solution is absorbed onto a carrier layer of porous absorbent material that is placed into a reservoir in the control wand then sealed with a frangible environmental seal, such as a thin aluminum foil. It is also understood that the control material could be placed directly into the cavity in the control wand and sealed without a carrier. Instead of a wand-type delivery device of the type previously described, the control material delivery device could come in the form of a:

blister filled with control material. The foil sealed blister could still be toed to initiate the test as described herein gel-cap filled with control material similar to gel-caps used to delivery drugs such as OTC pain reducers, or any other method of containing and automatically dispensing an appropriate dosage of control material.

An example of the above-mentioned alternative control material delivery devices is illustrated in FIGS. 9-13. This illustrated therein, a plurality of such devices 150 can be coupled or packaged together. Each individual control material delivery device 152 is separable by any suitable mechanism. For instance, the plurality of devices 160 can be provided with frangible areas 154 for separating the individual devices 152 from one another. The frangible areas 154 can be provided by any suitable mechanism, such as scoring or other weakening of the material in these areas.

Each individual control material delivery device 152 can be provided in any suitable form. According to the illustrated embodiment, each device 152 can comprise a body 156. The body 156 can take any suitable form. According to the illustrated embodiment, the body 156 is in the form of a strip-like member. The body 156 can be formed from any suitable material, such as a plastic, fibrous material, or composite.

Attached to the body 156 is a reservoir 158. The reservoir can be provided with any suitable construction. For example, the reservoir can be configured to mate with an opening provided in an analyte monitor or meter, for example, in the manner previously described in connection with the description of FIG. 4. Each reservoir 158 is configured to receive a control material 160 therein. Each reservoir 158 may also be provided with a seal 162 to maintain that control material 160 within the reservoir 158. The seal 162 can take any suitable form. For example, the seal 162, according to the illustrated embodiment, comprises a pierceable member such as a thin metal foil. Thus, the seal 162 may optionally be provided with a construction, which is pierceable by a member such as a hollow needle, as previously described in connection with the embodiment depicted in FIG. 4. Each device 152 may also be provided with a flange-like member 164 which is also attached to the body 156 of the device 152. The flange-like member 164 provides rigidity and support to the reservoir 158, and facilitates attachment thereof to the body 158.

The flange-like member 164 may also include a backing 166 which is not pierceable. Thus, for example, the backing 166 is not pierceable by a hollow needle. This construction of the backing 166 can be provided to protect the fingers of a user when the reservoir 158 is inserted into a meter or monitor, which includes a piercing element, such as a hollow needle, which is used to access the control material 160 within the reservoir 158.

Devices constructed according to further alternative embodiments of the present invention are depicted in FIGS. 14-30B. These devices have a construction and functionality which is similar to that of the previously described embodiments. Therefore, where a feature of the alternative embodiments finds a corresponding or feature in common with the previously described embodiments, they have been given similar reference numerals (e.g., 113 and 213). Therefore, reference is made to the previously described embodiments for supplemental description of these previously described features.

The devices and methods according to the embodiments depicted in FIGS. 14-30B have certain features in common. For instance, according to these alternative embodiments, the device 200 can possess a single piece construction, as opposed to a two-piece construction described according to other embodiment of the present invention. Each of these embodiments also may possess a reservoir constructed to retain a control material in flowable or liquid form, the provision of a porous or absorbent material as a carrier is not required, however, may be present according to further optional embodiments. These embodiments also possess a flexible neck construction which facilitates alignment and usage of the device, in particular by people with diabetes. The devices of these embodiments can also be made of any suitable material, such as, metal, wood, plastic, etc. According to one option, the device can be made of an injection molded plastic material to simplify production and reduce costs.

As illustrated, for example, in FIGS. 14-17, the first portion 212 of the device 200 is provided with a configuration which facilitates handling by a user. This is particularly important when the device 200 is intended for use with blood glucose monitors. This is because people with diabetes can lack tactile dexterity. Thus, the first portion 212 of the device 200 can be provided with any suitable form which facilitates grasp by a user.

Figure 15:
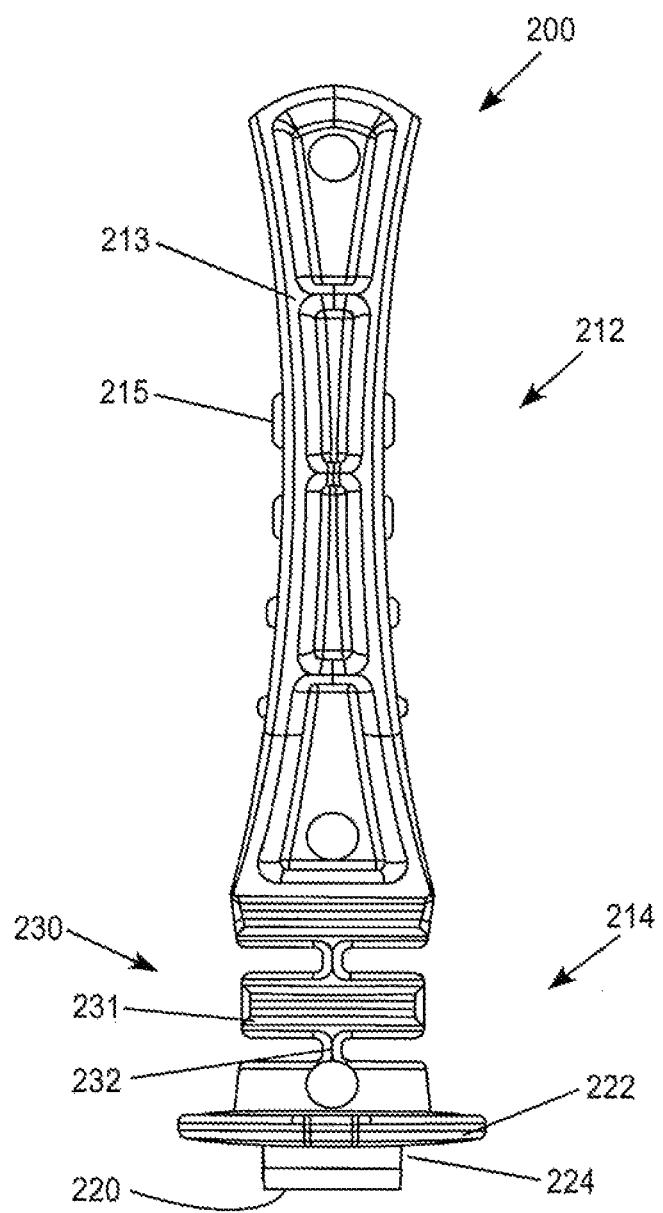
FIG. 15 is an edge view of the device of FIG. 14.
Figure 16:
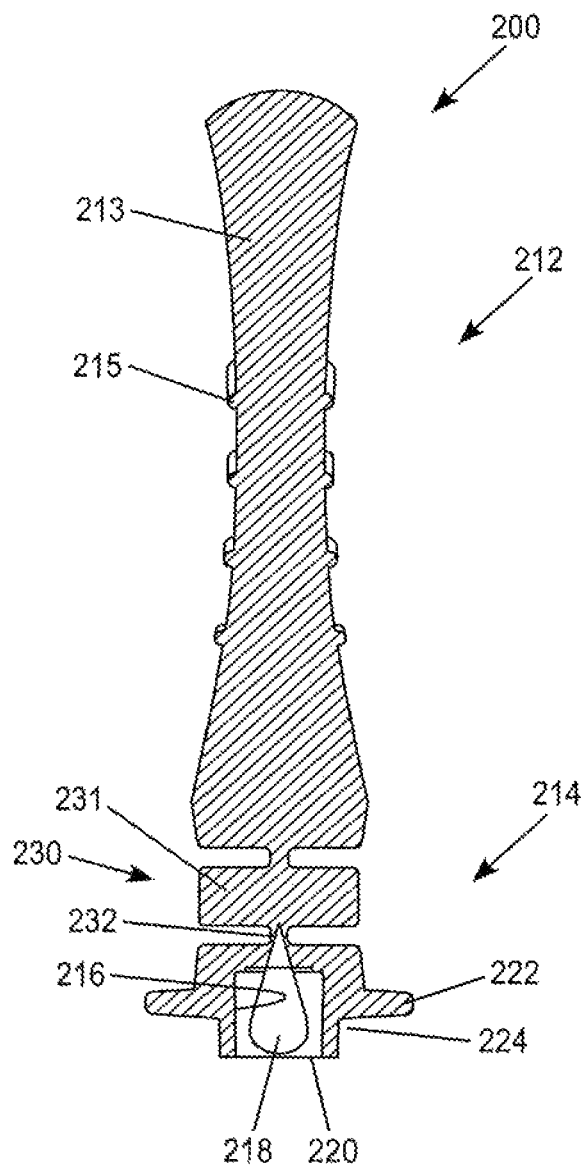
FIG. 16 is a longitudinal sectional view of the device of FIG. 14.
Figure 17:
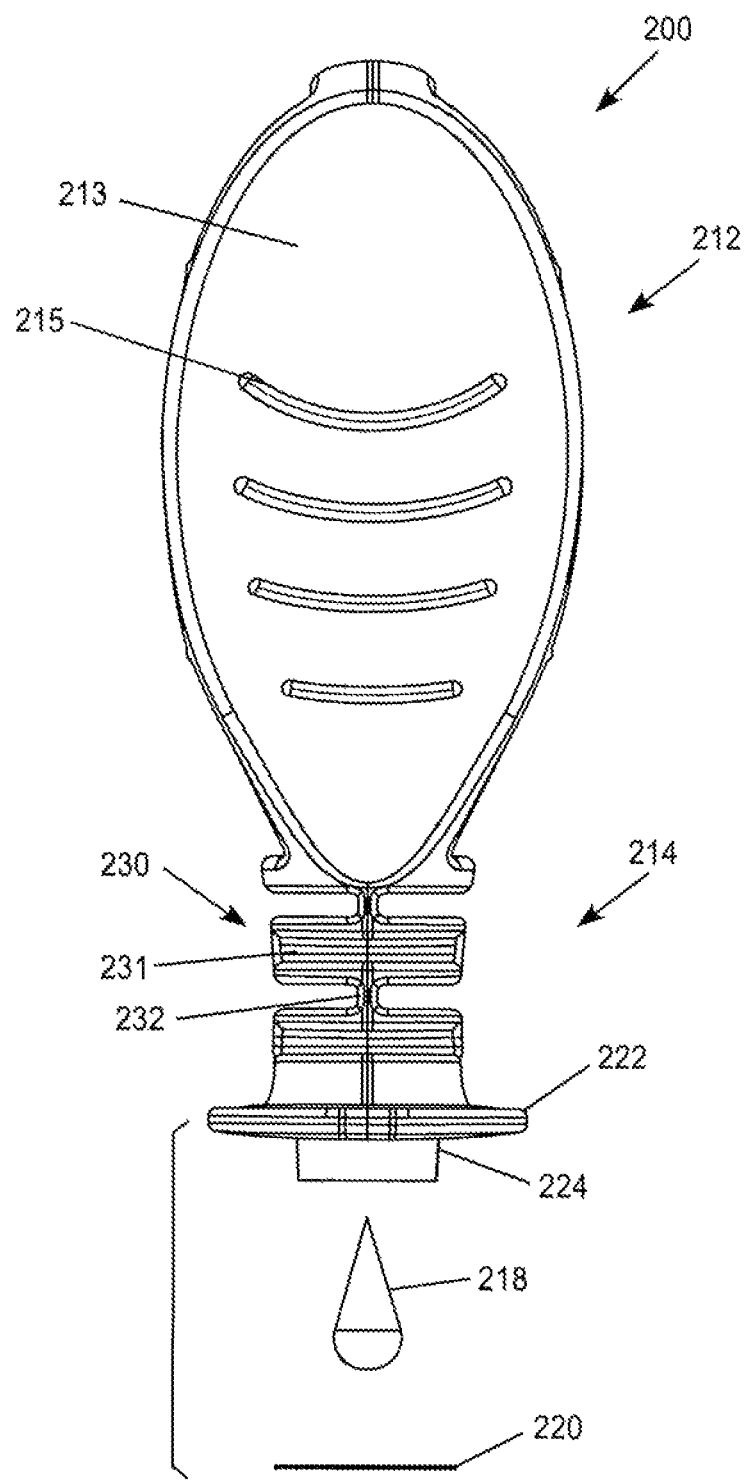
FIG. 17 is an exploded view of the device of FIG. 14.

According to the illustrated embodiment, the first portion 212 comprises a flattened relatively wide paddle-like shape. The paddle-like shape includes facing surfaces 213 which are contoured in an hourglass type manner such that the second portion 212 is provided with a cross-section that is relatively thin toward the middle, and wider towards its ends (FIGS. 15-16). The first portion 212 may optionally be provided with a feature that reduces slippage. For example, according to the nonlimiting illustrated embodiment, the first portion 212 is provided with a series of raised projections or ribs 215. Alternative features, such as a high friction surface coating or material disposed on all or a portion of surfaces 213 and/or ribs 215 may also be provided.

The device 200 may further include a second portion 214 with a flexible neck construction 230. The flexible neck 230 facilitates usage of the device by permitting relative movement between the first portion 212 and second portion 214 of the device. The flexible neck 230 can facilitate use of the device 200 in connection with mating the body 224 with an opening in a meter. The relative movement between the first portion 212 and the second portion 214 facilitates keeping the flanged 222 body 224 pressed flat against the opening, thus improving the ability to form, a seal therewith. The flexible neck 230 may possess any suitable construction permits this desired relative movement. Thus, the flexible neck may simply comprise a relatively thin neck of flexible material or other alternative configurations. According to the illustrated examples, the flexible neck 230 comprises a series of sections 231 interconnected by one or more thin flexible necks 232.

The second portion 214 of the device 200 can define a reservoir 216, which; houses a control material 218, as described in connection with the previous embodiments. Optionally, the control material 218 can contain one or more target analytes having a known and/or predetermined concentration and can be in liquid or flowable form as illustrated in, for example, FIGS. 16-17. The reservoir 216 can be sealed by a corresponding closure or seal 220. The second portion 214 further comprises a flanged 222 body 224, configured in a manner similar to that of the previously described embodiment.

Figure 18:
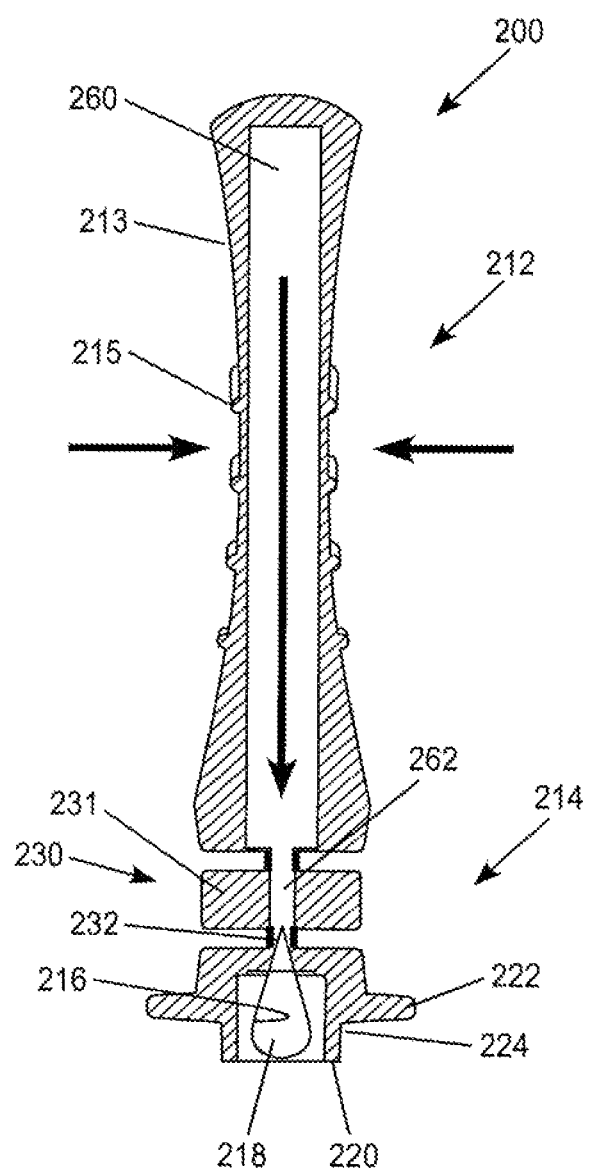
FIG. 18 is a longitudinal sectional view of an alternative embodiment of device according to the present invention.

According to certain alternative embodiments, the device 200 can include one or more features which allow the user to urge the control material out of the device so as to deliver it to its intended location. A number of such features are contemplated, including the use of positive and/or negative pressures. According to one nonlimiting, specific example, as illustrated in FIG. 18, the first portion 212 of the device 200 can comprise a hollow interior region 260. Further, the second portion 214 of the device may also comprise a hollow region 262, which is preferably in communication with the first hollow region 260. Thus, the use is able to grasp the handle 213 and squeeze in the direction of the horizontal arrows appearing in FIG. 18. This compression of hollow region 260 forces any air, or other fluid, contained therein in the direction of the vertical arrow. The forced fluid then travels through the second hollow region 262 and into the reservoir 216, where it then acts to force the control material 218 out the opening of the reservoir 216. It should be evident that any of the previously or subsequently described embodiments can be modified in a suitable manner, similar to that described above, to provide the same optional functionality.

As mentioned above, in the embodiments depicted in FIGS. 14-24 the first portion 212 in the second portion 214 are integrally formed or comprise a single-piece monolithic construction. However, the invention is not so limited and can be formed in multiple parts that are either permanently or releasably connected together.

It should be evident that the device 200 has a configuration such that it can be utilized in a manner similar to that described in connection with the previous embodiments.

Figure 19:
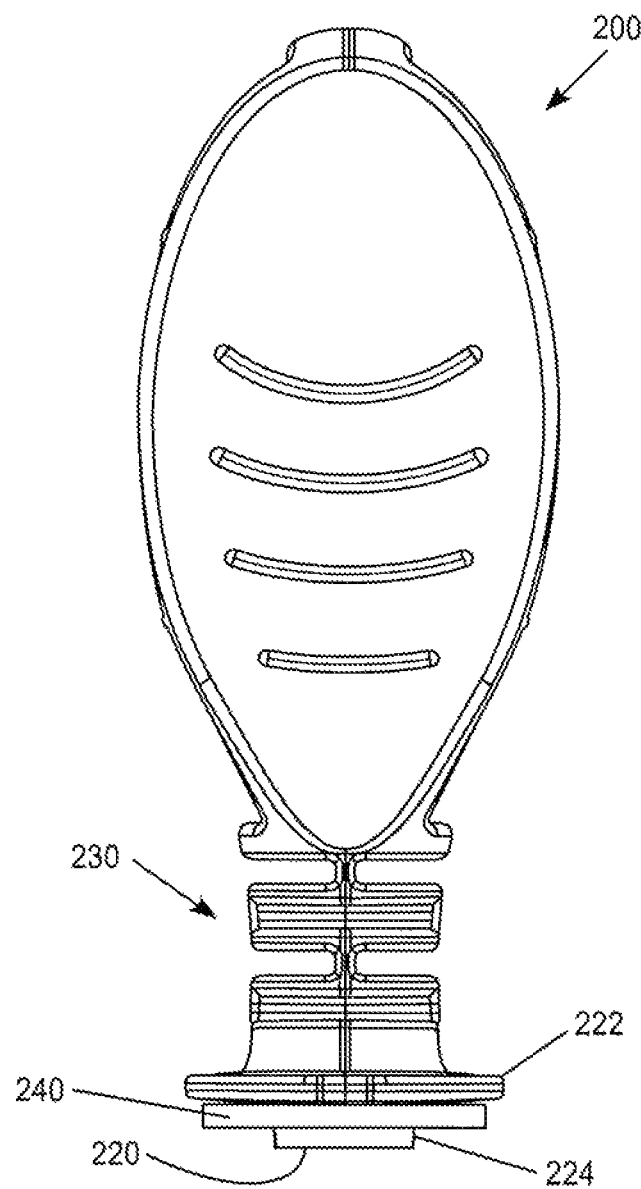
FIG. 19 is a side view of a further alternative embodiment of a device formed according to the present invention.
Figure 20:
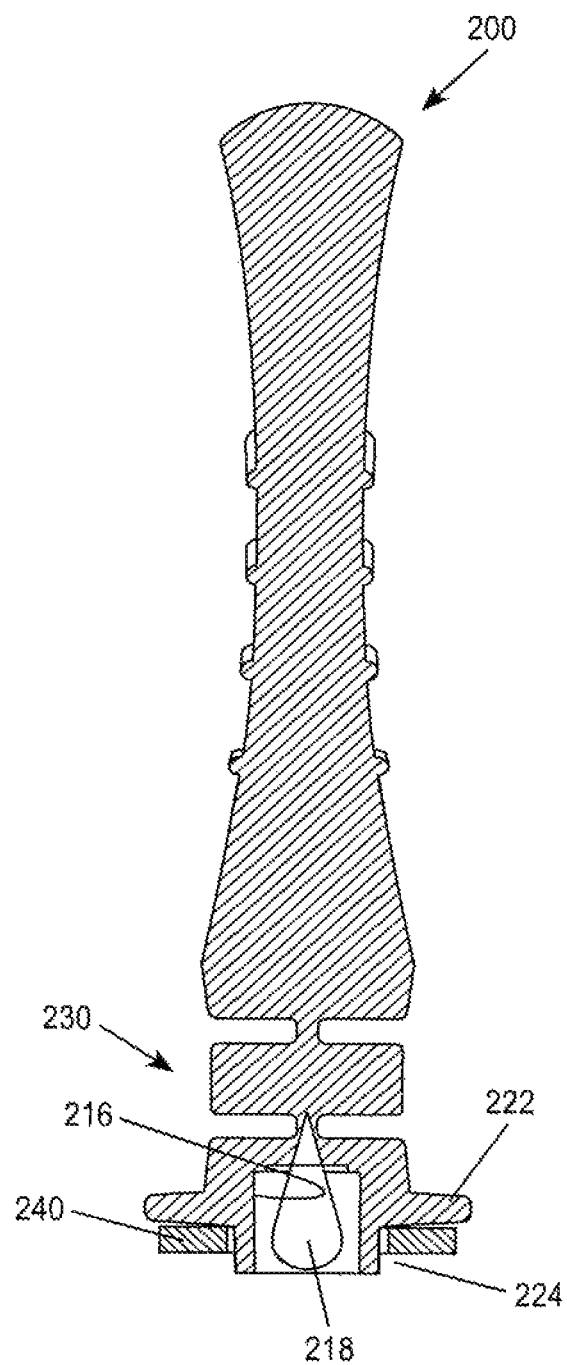
FIG. 20 is a longitudinal sectional view of the device of FIG. 19.

The device 200 illustrated in FIGS. 19-20 has the same features as the device 200 described above. As illustrated in FIGS. 19-20, the device 200 according to this alternative embodiment possesses a gasket or seal 240 disposed about the body 224 and abutting the flange 222. The gasket 240 can be formed from any suitable material, natural or synthetic. For example, the gasket 240 can be formed from foam, rubber, cork material, or a composite. The gasket 240 can be a separate component that is fitted over the body. When formed as a separate component, the gasket can be held in place by friction or by a suitable adhesive. Alternatively, the gasket 240 can be co-molded with the device 200 so as to be unified therewith. The gasket 240 enhances a seal formed between the flanged 222 body 224 when the device 200 is used in conjunction and mated with an opening of a meter, as will be described in greater detail herein.

Figure 21:
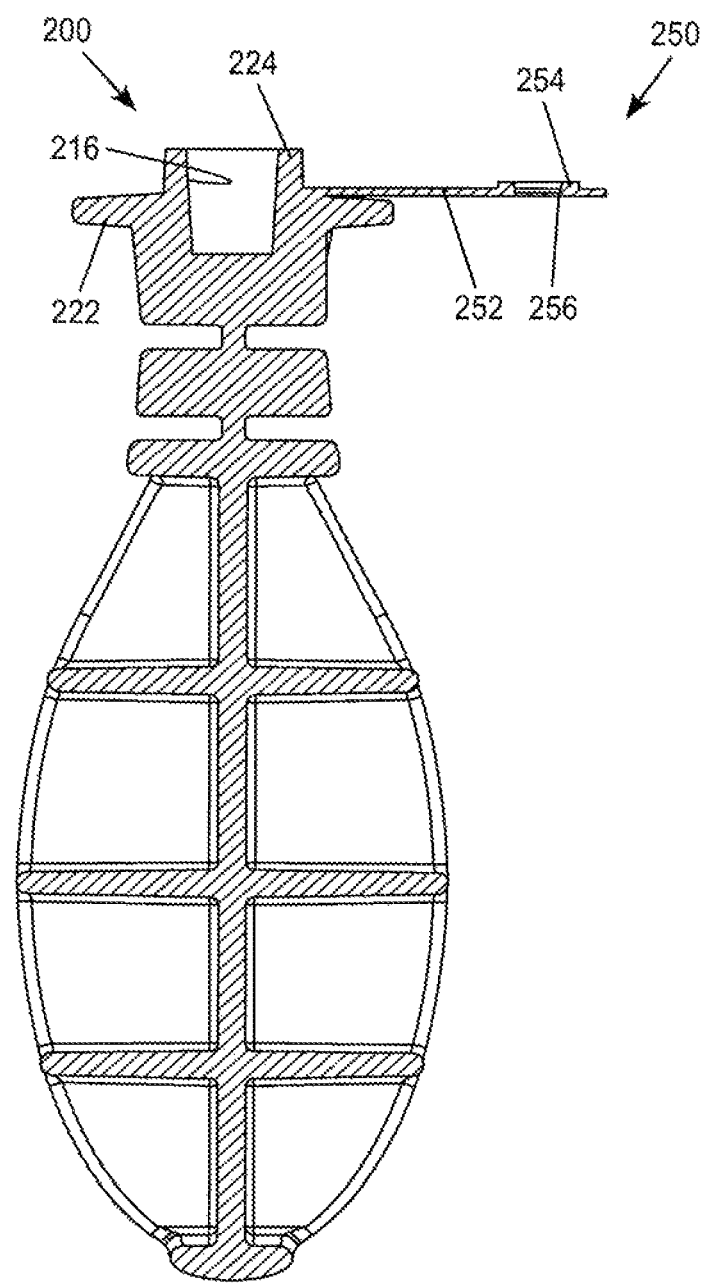
FIG. 21 is a longitudinal sectional view of an additional alternative embodiment of a device of the present invention in a first state.
Figure 22:
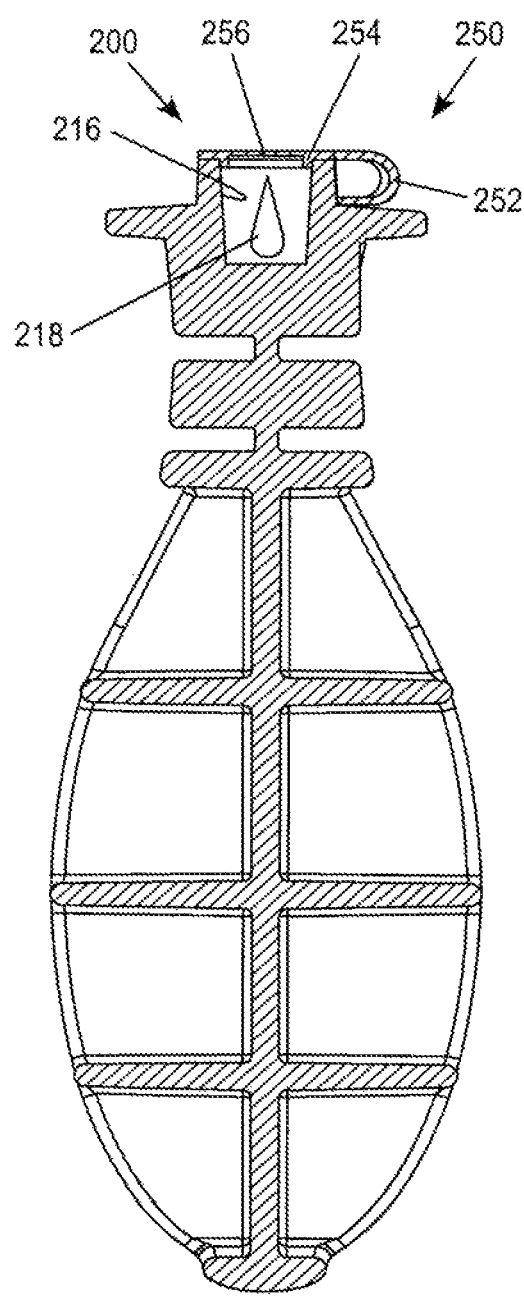
FIG. 22 is a longitudinal sectional view of the device of FIG. 20 in a second state.

The device 200 illustrated in FIGS. 21-22 has the same features as the device 200 described above. As illustrated in FIGS. 21-22, the device 200 according to this alternative embodiment possesses an alternative closure 250 for the reservoir 216. The alternative closure 250 can have any suitable construction. According to the optional illustrated embodiment the closure 250 comprises a handle or hinge 252 connected to the flanged 222 body 224. The hinge 252 can be connected in any suitable fashion. According to the illustrated embodiment, the hinge 252 is integrally formed with the flanged 222 body 224, such as by molding. Alternatively, the hinge may be separately formed and secured in place by adhesive, beat welding, ultrasonic welding or other suitable technique. The hinge may also include a ring or collar that fits around the body 224 to secure the hinge 252 in place. The closure 250 may further include a cap portion 254 that mates with reservoir 216 opening forming a seal therewith to contain the control material 218 contained therein (FIG. 16). According to one optional embodiment, the cap portion 254 can be pressed down and lifted up by a user to form a re-sealable closure. Alternatively, the cap portion 264 can be secured in place to the flanged 222 body 224 by adhesive, heat welding, ultrasonic welding, or other suitable technique. The cap portion may comprise a frangible portion 256. The frangible portion 256 can be constructed so that it is by a lancet, needle, or similar modality.

Figure 23:
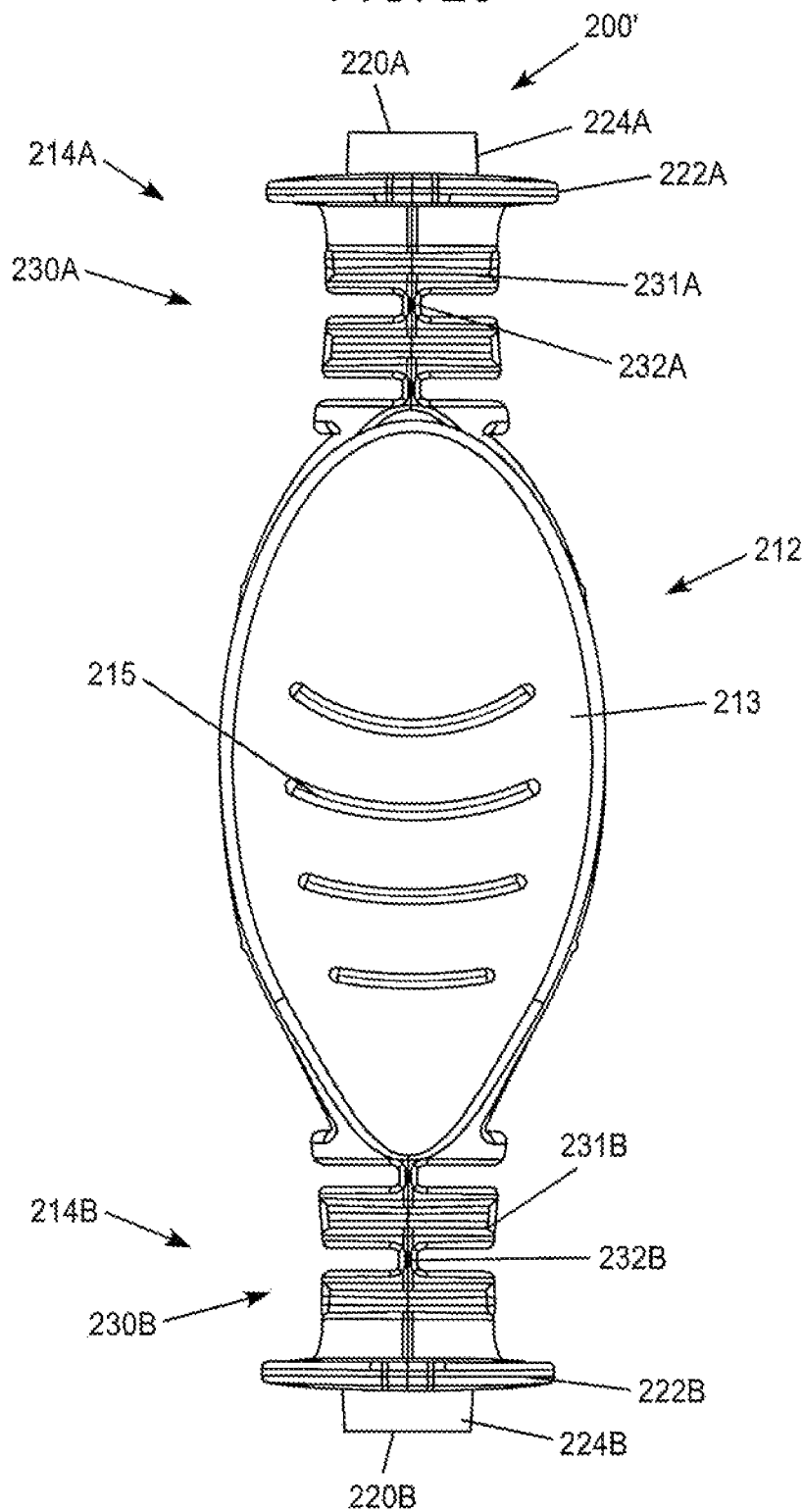
FIG. 23 is a side view of a yet another embodiment of a device formed according to the invention.
Figure 24:
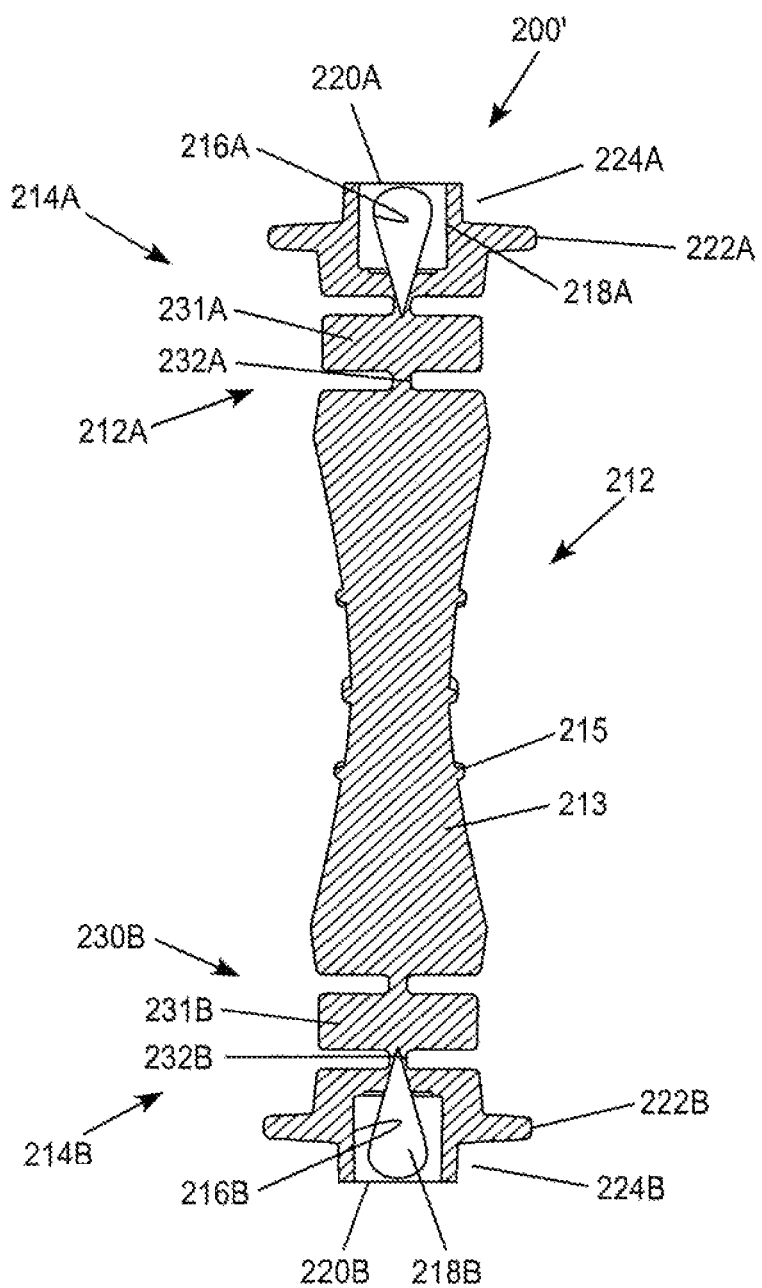
FIG. 24 is a longitudinal sectional view of the device of FIG. 23.

The device 200' illustrated in FIGS. 23-24 can share any combination or all of the same features as the device 200 of the previously described embodiments. The main distinction is that device 200' has two second portions 214A, 214B, each with a flexible neck construction 230A, 230B optionally provided with a construction previously described herein (components of the second portion 214A are labeled as in previous figures with "A" added to each label, and the components of the second portion 214B are labeled as in previous figures with "B" added to each label). Each second portion 214A, 214B of the device 200' defines a reservoir 216A, 216B which houses a control material 218A, 218B. The control material 218A, 218B can be essentially the same, thus providing the ability to perform at least two similar control tests with the same device 220'. As previously described, the control material may contain one or more target analyte(s). Alternatively, the control material 218A can differ from the control material 218B in one or more respects. For example, the first control material may contain a relatively lower concentration of a target analyte, while the second control material may contain a relatively higher concentration of the target analyte, thus providing a single device 200' with the ability to conduct a control test for both low and high analyte concentration ranges to ensure even greater accuracy of a meter or other measuring device. According to a further option, the control materials 218A, 218B can be used to perform a control test for at least two different target analytes. Thus, the first control material 218A can have a known concentration of a first analyte, while the second control material 218B can have a known concentration of a second analyte. The reservoirs 216A, 216B can be sealed by a corresponding closure or seal 220A, 220B, as illustrated. Alternatively, the closure can be constructed as illustrated and described above in connection with FIGS. 21-22. The second portions 214A, 214B can have either the same type of closure or seal, or different types of closures/seals.

Figure 25:
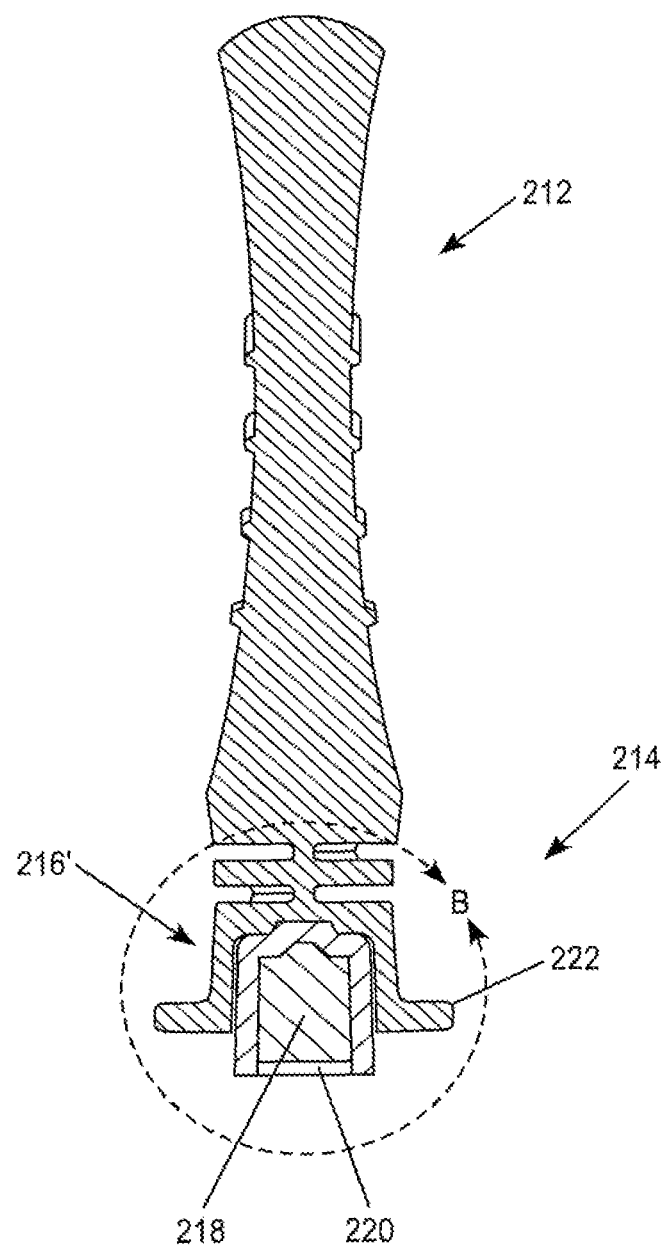
FIG. 25 is a sectional view of a further alternative embodiment of a device of the present invention.
Figure 26:
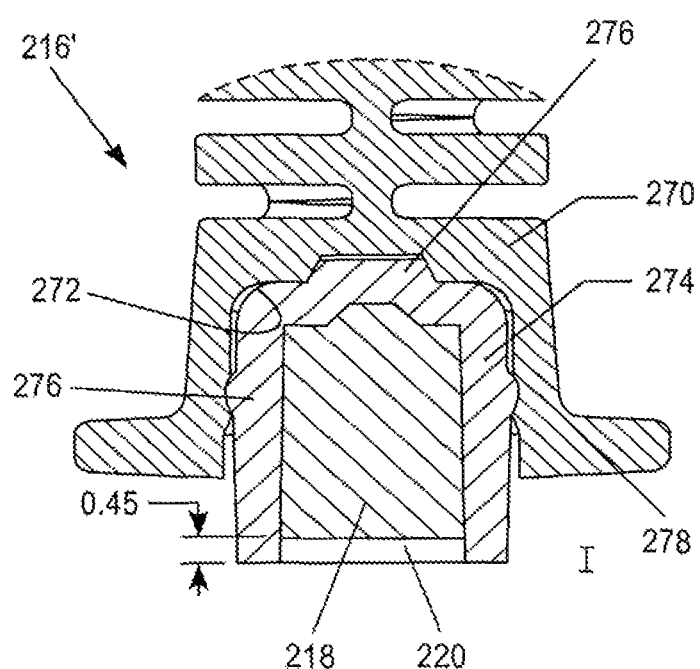
FIG. 26 is an enlargement of the detail of area B in FIG. 25.

According to further optional embodiments of the present invention, any of the previously or subsequently described embodiments can be modified so as to include an alternative reservoir construction, an example of which being illustrated in the embodiments depicted in FIGS. 25-26. As illustrated therein, the second portion 214 of the device includes a modified reservoir 216'. The modified reservoir 216' can be generally characterized as being in the form of a separable multi-piece construction. Such a construction can provide certain advantages. For example, the separable reservoir component containing the control material can be in the form of a cartridge which can be inserted into a reusable handle portion constituting the remainder of the device. Thus, once the control test has been conducted, the separable reservoir component containing control material can be removed and discarded appropriately. Such a construction may provide advantages in terms of cost and convenience as well as significantly reducing waste due to the reusability of the handle portion. Further, the separable reservoir component containing the control material can be formed of a material which is different in nature than that of the handle portion into which it is inserted. For instance, the separable reservoir component can be formed from a relatively low moisture vapor transmission rate (LMVTR) material. Thus, the control material is kept in a more stable manner that would be possible using a higher moisture vapor transmission rate material. To the extent that the LMVTR material is more costly than a relatively higher moisture vapor transmission rate material, cost savings can be obtained through the above-mentioned modified reservoir construction.

The above noted concepts can be executed in any suitable manner. According to the nonlimiting illustrated embodiment, the modified reservoir portion 216' comprises a lower member 270 defining a recess 272 therein. Received within a recess 272 is a separable reservoir component 274 containing the control material 218. The separable component may be closed by a frangible seal 220, as previously described. As noted above, this separable component 274 can be formed of any suitable material, such as a LMVTR plastic material. The separable component 274 can be retained within the recess 272 in any suitable fashion. Contemplated alternatives include adhesives, fasteners, and frictional retention. According to the illustrated embodiments, the separable component 274 is retained within the recess 272 by plurality of interacting frictional detents 276, 278.

Further aspects of the invention involves analyte testing/monitoring devices and methods including the devices (e.g., 100, 200, 200') of the type described above in, conjunction with an integrated analyte monitor or meter. The integrated monitor or meter optionally being capable of one or more of the following:

extracting the control material transporting the control material to an analysis site within the integrated monitor (e.g., as described in several of the integrated meter documents incorporated herein by reference)

analyzing the control material to determine the concentration of the analyte contained in the fluid analyzing the control to determine whether the sample is a body fluid or a control material comparing the result of the control test against a control calibration value, which may be read off a barcode, RFID, or similar device and/or stored in a memory of the monitor or meter, and displaying the result of the control test as a simple-to-interpret pass or fail result through simple audible/visual signals.

Figure 27:
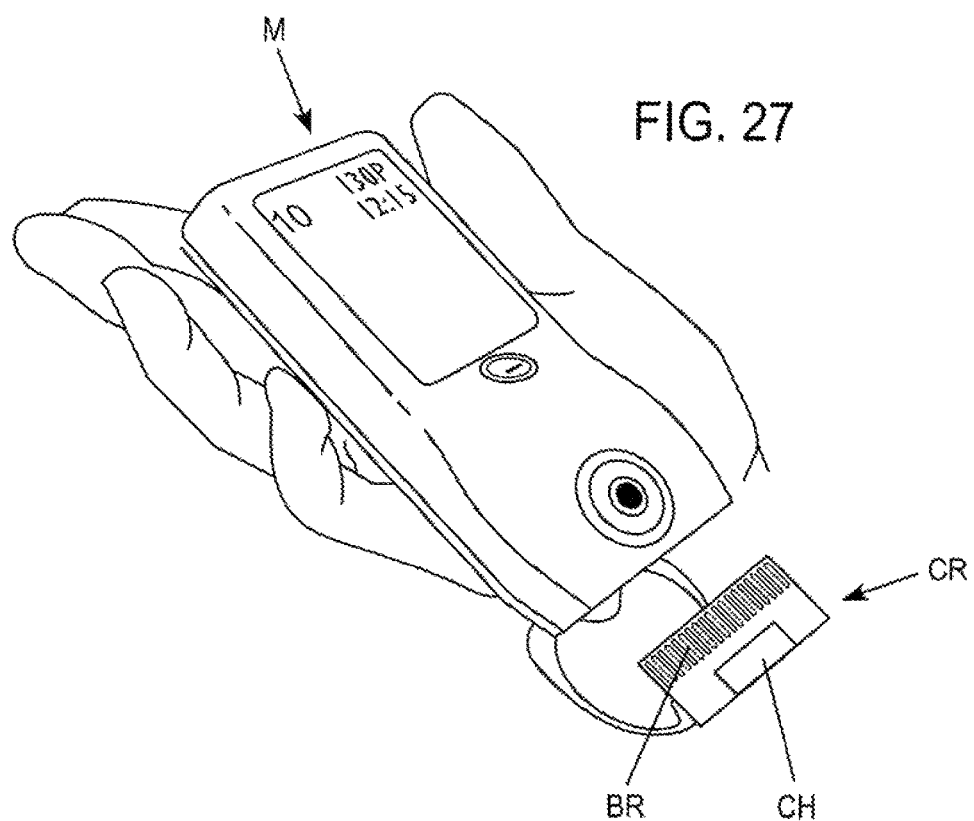
FIG. 27 is a schematic illustration of certain techniques and mechanisms for providing calibration information.

To complete the described steps automatically the analyte monitor should also have the capability of gathering calibration information automatically, such as from an analyte concentration measuring and analysis mechanism contained with the device. If analysis site(s) is/are contained within a single strip or multi-test cartridge CR, as illustrated in FIG. 27, the calibration information for the analyte concentration measuring and analysis mechanism(s) could be delivered to the meter or monitor M via a bar code BR, RFID chip CH or other mechanism.

One advantage of the invention is automated detection and marking of a control test to distinguish that test from, for example, a test involving a sample of body fluid. This can be accomplished by several methods; one method of identifying a control test is described as follows. The control material can be designed such that it reacts with the analysis site in a manner distinguishable from the reaction with a bodily fluid. For example, the viscosity of the control material can be so different, either lower or higher than the tested body fluid, that the rate of reaction or sample delivery can be used to distinguish control material from body fluid. Specifically, glucose monitors typically have stated hematocrit ranges that are acceptable for use with the device. As hematocrit increases the viscosity of blood also increases. The analysis site and method could be designed in such a manner that the rate of reaction is inversely related to hematocrit (higher hematocrit=slower reaction). This has been described, for example, in US 2006/0281187, the entire contents of which is incorporated herein by reference. To accomplish this, the control material used within the analysis site could be contained in a porous material. The size of the pores in the material can be used to control the rate of reaction. The control fluid can be designed such that its viscosity is lower than the equivalent viscosity of the lowest allowable hematocrit level. Therefore as the analysis is completed within the integrated monitor the rate of reaction can be used to identify control material tests.

Another method of identifying a control sample versus a body fluid sample involves adding identifying markets to the control material. For example, control material could be identified by optical detection by adding color within the detection wavelength such that a color change of an order of magnitude higher than physiologically possible given the kinetics of the assay occurs nearly instantaneously. The degree of color added via a dye or other colored means is enough to detect via this method, but not so much as to reduce the dynamic detection range of the system so that the proper level of analyte detection in the control material can correctly indicate system analyte recovery status as "Pass" or "Fail" through clear audible and/or visual signals. Another similar option that may be implemented is to provide the control material with a chemical marker that initially reacts with the analysis site to produce an initial spike in color indicating to the meter the presence of control solution. The initial color spike can be designed to quickly disappear. Subsequently, the analysis site reacts with the analyte(s) in a manner that can be read and interpreted to determine the concentration thereof.

Other similar methods of observing the time rate of change of the analysis site (reagent) are also comprehended, i.e., very, slow reaction, or reactions proceeding along known value vs. time plots, etc.

According to further alternative embodiments, the automated determination of a control solution test can be accomplished using algorithms executed by the electronic components within a monitor or meter.

A method performed according to the principles of one embodiment of the present invention includes one or more of the steps in FIGS. 27 and 28A-28D:\

Step 1: Provide calibration information to the monitor or device (e.g., FIG. 27 as described above).

Step 2: Use control material applicator (100, 200, 200') to deliver a dose of control material to monitor or device (M) (FIG. 28A). Note: The integrated monitor can optionally detect the presence of a "finger," in this case the control wand (100, 200, 200'), and automatically lances the closure (20, 120, 220, 256) and transports the control material (18, 118, 218) (e.g., FIG. 4).

Step 3: Integrated monitor analyzes the control material and determines that sample is a control test as indicated by any suitable symbol, such as the "check-mark" symbol on LCD (FIG. 28B). Alternatively, the monitor may provide an audible signal in place of, or in addition to the symbol.

Step 4a: Control material is analyzed and its analyte concentration value is displayed (e.g., 100 mg/dL) and compared against stored calibration values, in this example, the value is within the expected range and device displays any suitable symbol (280C), such as the "check" indicating "pass" (FIG. 28C). Alternatively, the monitor may provide an audible signal in place of, or in addition to, the symbol.

Step 4b: Control material is analyzed, the measured analyte concentration displayed and found to be outside of the expected range. In this case, the monitor indicates a failed test by displaying any suitable symbol (280D), such as crossed-out check mark. Alternatively, the monitor may provide an audible signal in place of, or in addition to, the symbol. Note the "i" symbol indicates that user should look at manual to see how to address the failed test (FIG. 28D).

An alternative method performed according to a further option embodiment is illustrated in FIGS. 27 and 29A-29D, and is described as follows.

Step 1: Provide calibration information to the monitor or device (e.g., FIG. 27 as described above).

Figure 29A:
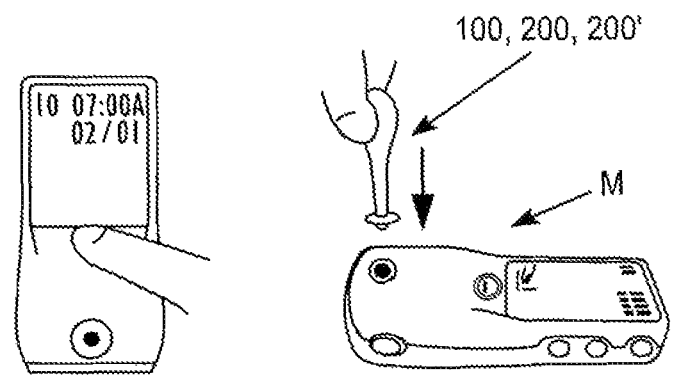
FIGS. 29A-29D illustrate an alternative method and possible uses of a device according to additional alternative embodiments of the present invention.
Figure 29B:
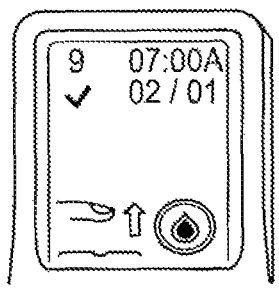

Step 2: Use control material applicator (100, 200, 200') to deliver a dose of control material (18, 118, 218) to monitor or device (M) (FIG. 29A). Note: The integrated monitor can optionally detect the presence of a "finger," in this case the control wand (100, 200, 200'), and automatically lances the closure (20, 120, 220, 256) and transports the control material (e.g., FIG. 4). The monitor M can optionally signal the user when the applicator can be removed from the opening.

Step 3: Integrated monitor analyzes the control material and determines that sample is a control test as indicated by any suitable symbol, such as the "check-mark" symbol on LCD (e.g., FIG. 29B). Alternatively, the monitor may provide an audible signal in place of or in addition to, the symbol.

Figure 29C:
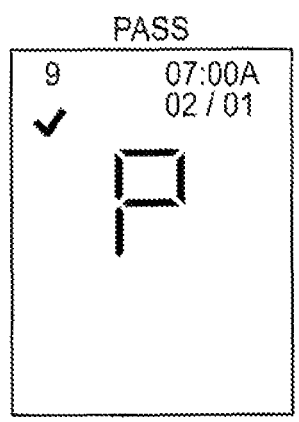

Step 4a: Control material is analyzed and its analyte concentration value is compared against stored calibration values. In this example, the value is within the expected range and device displays any suitable symbol, such as the "check" and a "P" indicating "pass" (FIG. 29C). Alternatively, the monitor may provide an audible signal in place of, or in addition to, the symbol. Additional and/or alternative visual and audible signals are contemplated. For example, the meter M can play a recorded spoken "pass" message. Note that unlike the previous embodiment, the concentration of analyte measured by the device is not displayed. It has been found that some users can become confused by the display of a concentration value and mistakenly assume it is a reading of the concentration of analyte in a sample of the user's body fluid, and engage in treatment (e.g., insulin dosage) based on this misunderstanding of the concentration value displayed by the meter M. This embodiment avoids such opportunity for misinterpretation.

Figure 29D:
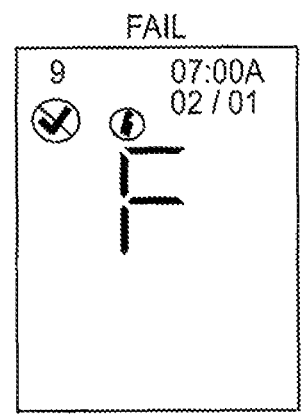

Step 4b: Control material is analyzed, the measured analyte concentration value is compared by the meter M against stored control or calibration values and found to be outside of the expected range. In this case the monitor displays a fail test. Any suitable symbol, such as the symbol indicated by the crossed check mark and "F," indicative of a failed control test. Additional and/or alternative visual and audible signals are contemplated. For example, the meter M can play a recorded spoken "fail" message. Note the "i" symbol indicates that user should look at manual to see how to address the failed test (FIG. 29D).

Figure 30A:
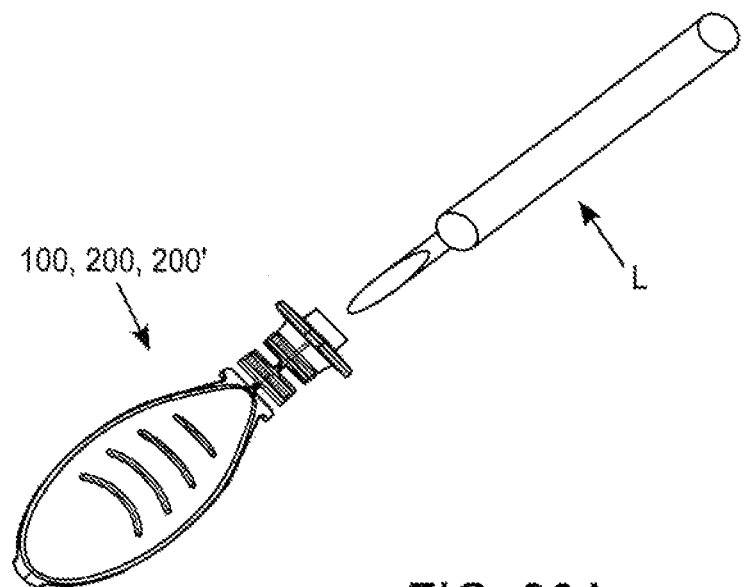
FIGS. 30A-30B illustrate an additional alternative method and possible uses of a device according to further alternative embodiments of the present invention.
Figure 30B:
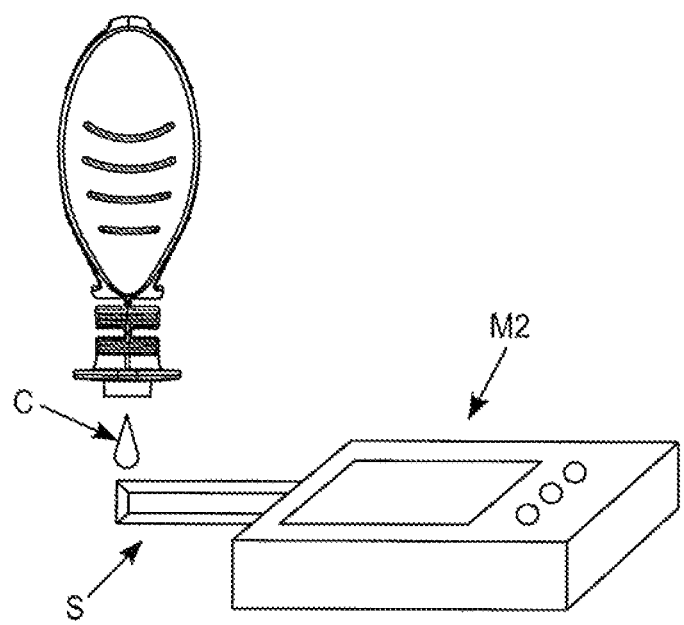

It should, be understood that the present invention is not limited to use of the devices (100, 200, 200') described herein with a particular type of meter or device. The present invention contemplates devices and methods that do not rely upon an integrated type meter or monitor. For example, many commercially available blood glucose monitoring systems include a lancing device, test strips and meter, one or more of which are separate components of the system. An arrangement and a control testing method performed according to an alternative embodiment of the present invention is illustrated in FIGS. 30A-30B. As illustrated therein, a device of the type described herein (100, 200, 200') contains a control material C. The control material C can have any suitable form or composition as previously described herein (18, 118, 218). The control material C is accessed by any suitable measure, such as by using a separate lancing device L that is commonly part of non-integrated blood glucose monitoring systems to pierce the closure or seal of the reservoir containing the control material C (FIG. 30A). A test strip S used for analyzing the concentration of a target analyte in a sample of body fluid by know techniques is inserted into a non-integrated meter M2. Using the device (100, 200, 200') the control material C is applied to a test strip S in a manner similar to how the user would introduce a sample of body fluid, such as blood obtained from a finger prick. The control material is then analyzed by the strip S and meter M2 in any suitable manner in order to verify whether or not the measured concentration of analyte in the control material C is within a tolerable expected range, and the results presented to the user. This can be done in any suitable manner, such as described herein in connection with previous embodiments.

According to one optional modification of the above described embodiment of FIGS. 30A-30B, instead of using the device (100, 200, 200') to apply the control material C directly to the test strip S, the control may be applied directly to the surface of a finger. The test strips is then brought into communication with the control material C on the finger, and is transported therein for analysis. This procedure more closely mimics a finger prick test using such non-integrated meters, and thus may be easier for the user to practice due to the familiarity of steps.

Numbers expressing quantities of ingredients, constituents, reaction conditions, and so forth used in this specification are to be understood as being modified in all instances by the term "about". Notwithstanding that the numerical ranges and parameters setting forth, the broad scope of the subject matter presented herein are approximations, the numerical values set forth are indicated as precisely as possible. Any numerical value, however, may inherently contain certain errors necessarily resulting from the standard deviation found in their respective measurement techniques. None of the elements recited in the appended claims should be interpreted as invoking 35 U.S.C. § 112, ¶6, unless the term "means" is explicitly used.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

We claim:

1. A method of verifying the accuracy of an analyte monitoring device through a control test, the method comprising:
   receiving control information from a test cartridge with the analyte monitoring device, wherein the control information comprises a range of analyte concentration values for a control solution;
   transporting the control solution to an analysis site in the test cartridge, wherein the control solution has a known and/or predetermined concentration of at least one analyte;
   determining the presence of the control solution using the analyte monitoring device, wherein determining the presence of the control solution comprises identifying the control solution;
   analyzing the control solution to measure the concentration of the at least one analyte contained therein;
   comparing the measured concentration of the at least one analyte with the control information to determine if the measured concentration corresponds to the range of concentration values obtained from the control information; and
   providing a pass or fail signal to indicate whether the measured concentration falls within the range of analyte concentration values.

2. The method of claim 1 further comprising detecting the presence of a control solution device with the analyte monitoring device.

3. The method of claim 1 further comprising lancing a control solution device with the analyte monitoring device to extract the control solution therein.

4. The method of claim 1 wherein identifying the control solution comprises analyzing the control solution using a colorimetric technique.

5. The method of claim 1 wherein identifying the control solution comprises analyzing the rate of reaction of the solution material.

6. The method of claim 1 wherein identifying the control solution comprises analyzing the wavelength of the control solution.

7. The method of claim 1 wherein the at least one analyte comprises glucose.

8. The method of claim 1 wherein the test cartridge comprises a multi-test cartridge.

9. The method of claim 1 wherein the control information is contained in a barcode or RFID chip associated with the test cartridge.

10. The method of claim 1 further comprising storing the control information in a memory of the analyte monitoring device.

11. The method of claim 1 wherein the analysis site comprises a reagent.

12. A system for verifying the accuracy of an analyte monitoring device through a control test, the system comprising:
   an analyte monitoring device comprising a non-transitory memory and a processor, wherein the non-transitory memory is programmed with instructions that cause the processor to:
   receive control information from a test cartridge, wherein the control information comprises a range of analyte concentration values for a control solution;
   determine the presence of the control solution by identifying the control solution, wherein the control solution has a known and/or predetermined concentration of at least one analyte;
   analyze the control solution to measure the concentration of the at least one analyte contained therein;
   compare the measured concentration of the at least one analyte with the control information to determine if the measured concentration corresponds to the range of analyte concentration values obtained from the control information; and
   provide a pass or fail signal to indicate whether the measured concentration falls within the range of concentration values.

13. The system of claim 12 further comprising a control solution device containing the control material therein.

14. The system of claim 13 wherein the analyte monitoring device is configured to detect the presence of the control solution device.

15. The system of claim 13 wherein the analyte monitoring device is configured to lance the control solution device to extract the control solution.

16. The system of claim 12 wherein the instructions that cause the processor to determine the presence of the control solution comprise instructions that cause the processor to analyze the control solution using a colorimetric technique.

17. The system of claim 12 wherein the instructions that cause the processor to determine the presence of the control solution comprise instructions that cause the processor to analyze the rate of reaction of the control solution.

18. The system of claim 12 wherein the instructions that cause the processor to determine the presence of the control solution comprise instructions that cause the processor to analyze the wavelength of the control solution.

19. The system of claim 12 wherein the at least one analyte comprises glucose.

20. The system of claim 12 further comprising a test cartridge.

21. The system of claim 20 wherein the test cartridge comprises a multi-test cartridge.

22. The system of claim 20 wherein the information is contained in a barcode or RFID chip associated with the test cartridge.

23. The system of claim 12 wherein the analyte monitoring device is configured to store the control information in the non-transitory memory.

* * * * *